US007613307B2

(12) United States Patent
Ohnishi et al.

(10) Patent No.: US 7,613,307 B2
(45) Date of Patent: Nov. 3, 2009

(54) ACTIVE SOUND REDUCTION APPARATUS AND ACTIVE NOISE INSULATION WALL HAVING SAME

(75) Inventors: Keizo Ohnishi, Takasago (JP); Masaharu Nishimura, Takasago (JP); Susumu Teranishi, Kobe (JP); Takanori Arai, Takasago (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 490 days.

(21) Appl. No.: 11/481,044

(22) Filed: Jul. 6, 2006

(65) Prior Publication Data

US 2006/0251267 A1 Nov. 9, 2006

Related U.S. Application Data

(62) Division of application No. 09/838,329, filed on Apr. 20, 2001, now abandoned.

(30) Foreign Application Priority Data

Apr. 21, 2000 (JP) ............................ 2000-120617
Jan. 26, 2001 (JP) ............................... 2001-18315

(51) Int. Cl.
*A61F 11/06* (2006.01)
*G10K 11/16* (2006.01)
*H03B 11/00* (2006.01)
*G10K 11/00* (2006.01)

(52) U.S. Cl. ...................... 381/71.1; 381/73.1; 181/210

(58) Field of Classification Search ................ 381/73.1, 381/72, 71.1–71.4; 181/206, 210, 284, 286
See application file for complete search history.

(56) References Cited

U.S. PATENT DOCUMENTS

| | | | | |
|---|---|---|---|---|
| 4,436,179 | A | | 3/1984 | Yamamoto et al. |
| 5,446,790 | A | | 8/1995 | Tanaka et al. |
| 5,475,761 | A | | 12/1995 | Eatwell et al. |
| 5,678,364 | A | | 10/1997 | Shima et al. |
| 5,724,432 | A | * | 3/1998 | Bouvet et al. .............. 381/71.1 |
| 5,930,371 | A | | 7/1999 | Cheng et al. |
| 6,006,858 | A | | 12/1999 | Shima et al. |
| 6,041,125 | A | | 3/2000 | Nishimura et al. |

FOREIGN PATENT DOCUMENTS

| | | | |
|---|---|---|---|
| DE | 19509678 | C1 | 5/1996 |
| EP | 0765968 | A1 | 4/1997 |
| JP | 3-217199 | A | 9/1991 |
| JP | 4-500 | A | 1/1992 |
| JP | 4-46115 | U | 4/1992 |

(Continued)

*Primary Examiner*—Xu Mei
(74) *Attorney, Agent, or Firm*—Birch, Stewart, Kolasch & Birch, LLP

(57) ABSTRACT

An active noise insulation wall includes an active sound reduction apparatus disposed on an upper end surface of a noise insulation wall. The active sound reduction apparatus comprises a combination of an active acoustic control cell and a sound tube. The active acoustic control cell controls a coming noise such that a diffracted sound pressure component of the coming noise at the upper end surface of the noise insulation wall is actively reduced. The sound tube decreases a sound wave of a frequency different from a target frequency of the active acoustic control cell. Thus, the active noise insulation wall can effectively reduce noises including many frequency components.

12 Claims, 22 Drawing Sheets

FOREIGN PATENT DOCUMENTS

| | | | |
|---|---|---|---|
| JP | 4-336795 | A | 11/1992 |
| JP | 5-257484 | A | 10/1993 |
| JP | 7-20880 | A | 1/1995 |
| JP | 8-85921 | A | 4/1996 |
| JP | 8-314474 | A | 11/1996 |
| JP | 9-44167 | A | 2/1997 |
| JP | 9-501779 | A | 2/1997 |
| JP | 9-119114 | A | 5/1997 |
| JP | 2639393 | B2 | 5/1997 |
| JP | 9-281977 | A | 10/1997 |
| JP | 10-37342 | A | 2/1998 |
| JP | 10-268873 | A | 10/1998 |
| JP | 11-256523 | A | 9/1999 |
| WO | WO-95/20841 | A1 | 8/1995 |
| WO | WO-98/37541 | A1 | 8/1998 |

* cited by examiner

ACTIVE SOUND REDUCTION APPARATUS AND ACTIVE NOISE INSULATION WALL HAVING SAME

This application is a Divisional of application Ser. No. 09/838,329, filed on Apr. 20, 2001, now abandoned the entire contents of which are hereby incorporated by reference and for which priority is claimed under 35 U.S.C. §120.

The entire disclosure of Japanese Patent Application No. 2001-18315 filed on Jan. 26, 2001 including specification, claims, drawings and summary is incorporated herein by reference in its entirety.

BACKGROUND OF THE INVENTION

1. Field of the Invention

This invention relates to an active sound reduction apparatus, and an active noise insulation wall having it. More specifically, the invention relates to an active sound reduction apparatus which is laid along highways, ordinary roads, and railways, and which is useful in insulating noises caused by traveling vehicles, trains, etc. as sound sources.

2. Description of the Related Art

To insulate noise from a sound source, such as a vehicle or a train traveling on a highway, an ordinary road, or a railway, a noise insulation wall is erected along such a highway or the like. In recent years, an active acoustic control cell has been developed as an effective insulator of noise produced in such a case. The active acoustic control cell senses a sound from a sound source by a microphone, and processes an electric signal based thereon to generate a sound from a speaker so that a sound pressure at a predetermined position is reduced to zero, thereby reducing noise which is propagated after diffraction from the sound source to the outside of a noise insulation wall. That is, this type of active acoustic control cell is disposed on an upper end surface of the noise insulation wall, a vertical wall provided along a road or the like. This active acoustic control cell performs control in such a manner as to decrease a diffracted sound pressure component (at the upper end surface) of coming noise by active means (see, for example, Japanese Unexamined Patent Publication No. 1997-119114).

FIG. 27 is an explanation drawing conceptually showing an example of an active noise insulation wall having such an active acoustic control cell. As shown in the drawing, a plurality of the active acoustic control cells A are disposed on an upper end surface of a noise insulation wall B, a vertical wall, along a longitudinal direction of the noise insulation wall B. The active acoustic control cell A has a structure in which a speaker 2 being a sound wave generator, an amplifier 3, a skin material 4, a microphone 5 being a sound detector, and a control circuit 6 are integrated into a casing 1. The speaker 2 is opposed to the skin material 4 so that a sound wave generated by the speaker 2 is incident on the skin material 4. The microphone 5 is installed at a position between the skin material 4 and the speaker 2. Thus, the speaker 2 outputs an electric signal corresponding to a sound wave detected by the microphone 5. Based on the electric signal, the control circuit 6 performs predetermined computation, and issues a control signal obtained thereby to the amplifier 3. The amplifier 3 sends a drive signal corresponding to the control signal to the speaker 2. The speaker 2 generates a sound wave corresponding to the drive signal. Transfer characteristics G based on the characteristics of the speaker 2, amplifier 3, microphone 5 and control circuit 6 is adjusted to negative infinity or a value close to negative infinity, or −1, or a value close to −1, so that control is performed over a broad range of frequencies. That is, the control circuit 6 stores a pattern of the transfer characteristics G at each frequency, performs required computations in response to electric signals sent from the microphone 5, and feeds predetermined control signals to the amplifier 3. The transfer characteristics G is controlled in this manner. Thus, if the sound pressure acting on the microphone 5 is designated as P, and a control sound pressure produced by the speaker 2, as Pc, then $Pc=G\cdot P$ holds. As a result, the sound pressure of a diffracted sound originating from a noise source (e.g., a driveway side), changing in direction at the upper end surface of the noise insulation wall B upon diffraction, and leaking to an opposite side of the noise insulation wall B (e.g., a private house side) can be decreased.

FIG. 27 shows an example of only one row of the active acoustic control cells A disposed along the noise insulation wall B. There is no restriction on the number of rows of the active acoustic control cells A. The number of rows of the active acoustic control cells A can be determined, as desired, according to the level of the noise to be decreased. An active noise insulation wall according to an earlier technology, having three rows of the active acoustic control cells A disposed thereon, is shown in FIG. 28. As the drawing shows, in this type of active noise insulation wall, three of the active acoustic control cells A are arranged in a horizontal direction perpendicular to a longitudinal direction of the noise insulation wall B, without spacing between the adjacent active acoustic control cells.

In the active noise insulation wall according to the earlier technologies, as described above, it induces a cost increase to broaden the frequency band targeted by the active acoustic control cell, or to provide a plurality of the active acoustic control cells. That is, the conventional active noise insulation wall is not sufficient for reducing nose effectively at a low cost.

SUMMARY OF THE INVENTION

The present invention has been accomplished in consideration of the above-described problems with the earlier technologies. The present invention provides an active sound reduction apparatus which can reduce noise rationally at a low cost, and which can reduce not only a diffracted sound, but also a sound directly transmitted from a noise source, and an active noise insulation wall having the active sound reduction apparatus.

One aspect of the present invention provides:

1) An active sound reduction apparatus having an active acoustic control cell, disposed on an upper end surface of a noise insulation wall, for controlling a coming noise such that a diffracted sound pressure component of the coming noise at the upper end surface is actively reduced; and one sound tube or a plurality of sound tubes of a length which is nearly ¼ of a wavelength or wavelengths of one sound wave or a plurality of sound waves other than a control target frequency of the active acoustic control cell, the one sound tube or the plurality of sound tubes being provided on a side of the active acoustic control cell facing a sound source to be subjected to sound reduction, or on a side of the active acoustic control cell opposite to the sound source, or on both of the sound source side and the opposite side of the active acoustic control cell.

According to this aspect, sound waves of frequencies different between the active acoustic control cell and the sound tube(s) can be decreased. Thus, noises including a wide range of frequency components can be reduced effectively.

2) The active sound reduction apparatus of the aspect 1), wherein a sound absorption material is disposed at a bottom of the sound tube to avoid an amplifying effect on a sound wave corresponding to a length which is nearly a half of a wavelength of a sound wave whose sound pressure is decreased by the sound tube.

According to this aspect, the sound tube decreases a sound wave of a frequency natural to the sound tube, while the sound absorption material absorbs a sound wave of a hazardous frequency deteriorating this sound wave decreasing effect. Thus, the aspect 2) can reduce noises, including a broad range of frequency components, more effectively than the aspect 1).

3) The active sound reduction apparatus of the aspect 1), wherein an acoustic resistor, such as a porous plate, is disposed inside the sound tube to avoid an amplifying effect on a sound wave corresponding to a length which is nearly a half of a wavelength of a sound wave whose sound pressure is decreased by the sound tube.

According to this aspect, the sound tube decreases a sound wave of a frequency natural to the sound tube, while the acoustic resistor decreases a sound wave of a hazardous frequency deteriorating this sound wave decreasing effect. Thus, the aspect 3) can reduce noises, including a broad range of frequency components, more effectively than the aspect 1).

4) The active sound reduction apparatus of the aspect 1), wherein an acoustic resonator is disposed inside the sound tube to avoid an amplifying effect on a sound wave corresponding to a length which is nearly a half of a wavelength of a sound wave whose sound pressure is decreased by the sound tube.

According to this aspect, the sound tube decreases a sound wave of a frequency natural to the sound tube, while the acoustic resonator decreases a sound wave of a hazardous frequency deteriorating this sound wave decreasing effect. Thus, the aspect 4) can reduce noises, including a broad range of frequency components, more effectively than the aspect 1).

5) An active sound reduction apparatus having an active acoustic control cell, disposed on an upper end surface of a noise insulation wall, for controlling a coming noise such that a diffracted sound pressure component of the coming noise at the upper end surface is actively reduced; and one acoustic resonator or a plurality of acoustic resonators tuned to a frequency or frequencies other than a control target frequency of the active acoustic control cell in order to decrease a sound pressure at the frequency or frequencies, the one acoustic resonator or the plurality of acoustic resonators being provided on a side of the active acoustic control cell facing a sound source to be subjected to sound reduction, or on a side of the active acoustic control cell opposite to the sound source, or on both of the sound source side and the opposite side of the active acoustic control cell.

According to this aspect, the sound pressure at a specific frequency other than the control frequency of the active acoustic control cell can also be decreased by the acoustic resonator(s). Thus, the aspect 5) can achieve satisfactory reduction of coming noise by the combined sound pressure decreasing function of the active acoustic control cell and the acoustic resonator(s).

6) An active sound reduction apparatus comprising a plurality of the active sound reduction apparatuses of the aspect 1) combined together.

According to this aspect, a plurality of the active acoustic control cells exhibit respective sound reducing functions. Thus, the aspect 6) can reduce noises, including a broad range of frequency components, more effectively than the aspect 1).

7) An active sound reduction apparatus comprising a plurality of the active sound reduction apparatuses of the aspect 2) combined together.

According to this aspect, a plurality of the active acoustic control cells exhibit respective sound reducing functions. Thus, the aspect 7) can reduce noises, including a broad range of frequency components, more effectively than the aspect 2).

8) An active sound reduction apparatus comprising a plurality of the active sound reduction apparatuses of the aspect 3) combined together.

According to this aspect, a plurality of the active acoustic control cells exhibit respective sound reducing functions. Thus, the aspect 8) can reduce noises, including a broad range of frequency components, more effectively than the aspect 3).

9) An active sound reduction apparatus comprising a plurality of the active sound reduction apparatuses of the aspect 4) combined together.

According to this aspect, a plurality of the active acoustic control cells exhibit respective sound reducing functions. Thus, the aspect 9) can reduce noises, including a broad range of frequency components, more effectively than the aspect 4).

10) An active sound reduction apparatus comprising a plurality of the active sound reduction apparatuses of the aspect 5) combined together.

According to this aspect, a plurality of the active acoustic control cells exhibit respective sound reducing functions. Thus, the aspect 10) can reduce noises, including a broad range of frequency components, more effectively than the aspect 5).

11) An active noise insulation wall comprising a plurality of the active sound reduction apparatuses of any one of the aspects 1) to 10), the active sound reduction apparatuses being disposed in a row along a longitudinal direction of an upper end surface of a noise insulation wall or a side surface of an upper portion of the noise insulation wall.

According to this aspect, sound waves of frequencies different between the active acoustic control cell and the sound tube(s) can be decreased. Thus, the aspect 11) can effectively reduce noises, including a wide range of frequency components, so that the function of the noise insulation wall can be improved.

12) The active noise insulation wall of the aspect 11), wherein the active sound reduction apparatuses are mounted on an upper portion of the noise insulation wall so as to be normally and reversely rotatable in a vertical plane.

According to this aspect, a region in which a diffracted sound is decreased can be determined arbitrarily by selecting, as desired, the angles of the active sound reduction apparatuses. Thus, the aspect 12) can obtain the most potent effect of reducing noises adapted for the location of installation, by using the noise insulation wall that can effectively reduce noises, including a wide range of frequency components.

13) The active noise insulation wall of the aspect 11), wherein at least one of the sound tubes of the active sound reduction apparatuses has a bottom portion entering a depression of an upper end portion of the noise insulation wall.

According to this aspect, an installation space for the sound tube can be secured in the noise insulation wall. Thus, the aspect 13) can decrease the bulk of the active noise insulation wall.

14) The active noise insulation wall of any one of the aspects 11) to 13), wherein the noise insulation wall branches at an upper end portion thereof to have a plurality of branch walls extending upward, and the active sound reduction apparatus is disposed either between two of the branch walls, or on a side of one of or the plurality of the branch walls facing a noise source, or on a side thereof opposite to the noise source.

According to this aspect, individual noise insulation functions are obtained by the branch walls. Thus, the aspect 14) can achieve a better noise insulation effect because the sound reducing effect of the branch wall is added.

15) An active noise insulation wall having a plurality of rows formed by spacing the adjacent rows by a predetermined distance, each of the rows being formed from a plurality of active acoustic control cells, disposed in a longitudinal direction of a noise insulation wall, for controlling a coming noise such that a diffracted sound pressure component of the coming noise at an upper end surface of the noise insulation wall is actively reduced.

According to this aspect, it is possible to obtain a more effective sound reducing effect than when there are provided a plurality of the rows of the active acoustic control cells disposed contiguously. Thus, the aspect 15) can achieve a satisfactory sound reducing effect by a fewer rows of the active acoustic control cells. Consequently, the active noise insulation wall can be constructed at a lower cost.

16) An active noise insulation wall having a plurality of rows formed by spacing the adjacent rows by a predetermined distance, each of the rows being formed from a plurality of the active sound reduction apparatuses of any one of the aspects 1) to 10), which are disposed in a longitudinal direction of the noise insulation wall.

According to this aspect, it is possible to obtain a more effective sound reducing effect than when there are provided a plurality of the rows of the active sound reduction apparatuses disposed contiguously. Thus, the aspect 16) can achieve a satisfactory sound reducing effect by a fewer rows of the active sound reduction apparatuses. Consequently, the active noise insulation wall can be constructed at a lower cost.

17) The active noise insulation wall of the aspect 15) or 16), wherein the distance between the active acoustic control cells or the active sound reduction apparatuses of the adjacent rows is adjustable.

According to this aspect, the distance between the adjacent active acoustic control cells or the adjacent active sound reduction apparatuses can be adjusted freely. Thus, the aspect 17) can easily secure an optimal spacing adapted for the installation place.

18) The active noise insulation wall of the aspect 15) or 16), wherein each of the rows of the active acoustic control cells or the active sound reduction apparatuses is mounted on an upper end portion of the noise insulation wall so as to be normally and reversely rotatable, and an angle of normal or reverse rotation of each row is adjusted, whereby the distance between the active acoustic control cells or the active sound reduction apparatuses of the adjacent rows is adjustable.

According to this aspect, the spacing between the adjacent active acoustic control cells or active sound reduction apparatuses can be adjusted by adjusting the angle of normal or reverse rotation. Thus, the aspect 18) can easily secure an optimal spacing adapted for the installation place.

19) The active noise insulation wall of the aspect 15) or 16), wherein noise killer cells are disposed, on one of the rows facing a noise source, for generating a sound wave interfering with a sound wave traveling rectilinearly from the noise source after passing over an upper end portion of the noise insulation wall to decrease the sound wave traveling rectilinearly.

According to this aspect, it is possible to decrease not only noise which diffracts at the upper end surface of the noise insulation wall and leaks to the outside, but also the sound wave traveling rectilinearly from the noise source, passing on the upper end surface of the noise insulation wall, and diffusing obliquely upwardly. Thus, the aspect 19) can reduce noises not only in a region below the noise insulation wall, but also in a region above the noise insulation wall, for example, a region covering an upper floor of a building.

20) The active noise insulation wall of the aspect 15) or 16), wherein composite noise killer cells having functions of a noise killer cell and the active acoustic control cell are disposed on one of the rows facing a noise source, the noise killer cell being adapted to generate a sound wave interfering with a sound wave traveling rectilinearly from the noise source after passing over an upper end portion of the noise insulation wall to decrease the sound wave traveling rectilinearly.

According to this aspect, it is possible to decrease not only noise which diffracts at the upper end surface of the noise insulation wall and leaks to the outside, but also the sound wave traveling rectilinearly from the noise source, passing on the upper end surface of the noise insulation wall, and diffusing obliquely upwardly. Thus, the aspect 20) can reduce noises not only in a region below the noise insulation wall, but also in a region above the noise insulation wall, for example, a region covering an upper floor of a building.

21) The active noise insulation wall of the aspect 19), wherein the noise killer cells each include noise detection means, such as a microphone, disposed on a straight line connecting the noise source to the upper end portion of the noise insulation wall, noise killer sound generation means, such as a speaker, for generating a sound wave interfering with a sound wave traveling rectilinearly along the straight line connecting the noise source to the upper end portion of the noise insulation wall to decrease the sound wave, and computation means for issuing a signal for generating a noise killer sound which is generated by the noise killer sound generation means based on noise detected by the noise detection means.

According to this aspect, the sound wave traveling rectilinearly from the noise source and diffusing to the outside of the noise insulation wall can be decreased by an active method. Thus, the aspect 21) can reduce noise in a region above the noise insulation wall satisfactorily.

22) The active noise insulation wall of the aspect 19), wherein the noise killer cell is an interference type muffler formed by combining a plurality of sound tubes.

According to this aspect, a sound wave traveling rectilinearly from a noise source and diffusing to the outside of the noise insulation wall can be decreased by a passive method. Thus, the aspect 22) can reduce noise in a region above the noise insulation wall by a simple structure and at a low cost.

23) The active noise insulation wall of the aspect 20), wherein the composite noise killer cells each include noise detection means, such as a microphone, disposed on a straight line connecting the noise source to the upper end portion of the noise insulation wall, one computation means for issuing a signal for generating a killer sound for noise based on the noise detected by the noise detection means, diffracted sound detection means, such as a microphone, for detecting a sound wave diffracting at the upper end portion of the noise insulation wall and leaking to an outside, other computation means for issuing a signal for generating a killer sound for a diffracted sound based on the diffracted sound detected by the diffracted sound detection means, mixing means for mixing the signal issued by the one computation means and the signal issued by the other computation means, and sound wave generation means, such as a speaker, driven by an output signal of the mixing means to generate a sound wave for decreasing both a sound wave traveling rectilinearly from the noise source and reaching the outside of the noise insulation wall, and a sound wave diffracting at the upper end portion of the noise insulation wall and reaching the outside.

According to this aspect, it is possible to decrease not only noise which diffracts at the upper end surface of the noise insulation wall and leaks to the outside, but also the sound wave traveling rectilinearly from the noise source, passing on the upper end surface of the noise insulation wall, and diffusing obliquely upwardly. Thus, the aspect 23) can reduce noise not only in a region below the noise insulation wall, but also in a region above the noise insulation wall, for example, a region covering an upper floor of a building.

24) The active noise insulation wall of any one of the aspects 15) to 23), wherein the noise insulation wall branches at an upper end portion thereof to have a plurality of branch walls extending upward, and one of or the plurality of the branch walls is or are formed only of a branch wall or branch walls having none of the active acoustic control cell, the active sound reduction apparatus, the noise killer cell, and the composite noise killer cell disposed thereon.

According to this aspect, individual noise insulation functions are obtained by the branch walls. Thus, the aspect 24) can achieve a better noise insulation effect because the sound reducing effect of the branch wall is added.

25) A composite noise killer cell including noise detection means, such as a microphone, disposed on a straight line connecting a noise source to an upper end portion of a noise insulation wall, one computation means for issuing a signal for generating a killer sound for noise based on the noise detected by the noise detection means, diffracted sound detection means, such as a microphone, for detecting a sound wave diffracting at the upper end portion of the noise insulation wall and leaking to an outside, other computation means for issuing a signal for generating a killer sound for a diffracted sound based on the diffracted sound detected by the diffracted sound detection means, mixing means for mixing the signal issued by the one computation means and the signal issued by the other computation means, and sound wave generation means, such as a speaker, driven by an output signal of the mixing means to generate a sound wave for decreasing both a sound wave traveling rectilinearly from the noise source and reaching the outside of the noise insulation wall, and a sound wave diffracting at the upper end portion of the noise insulation wall and reaching the outside.

According to this aspect, when the composite noise killer cell is mounted on the noise insulation wall, it can act on the diffracted sound and the rectilinear sound from the noise source to decrease both sound waves. Thus, the aspect 25) facilitates the construction of an active noise insulation wall for reducing noises not only in a region below the noise insulation wall, but also in a region above the noise insulation wall, and can contribute greatly to constructing the active noise insulation wall.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Figure 1A:
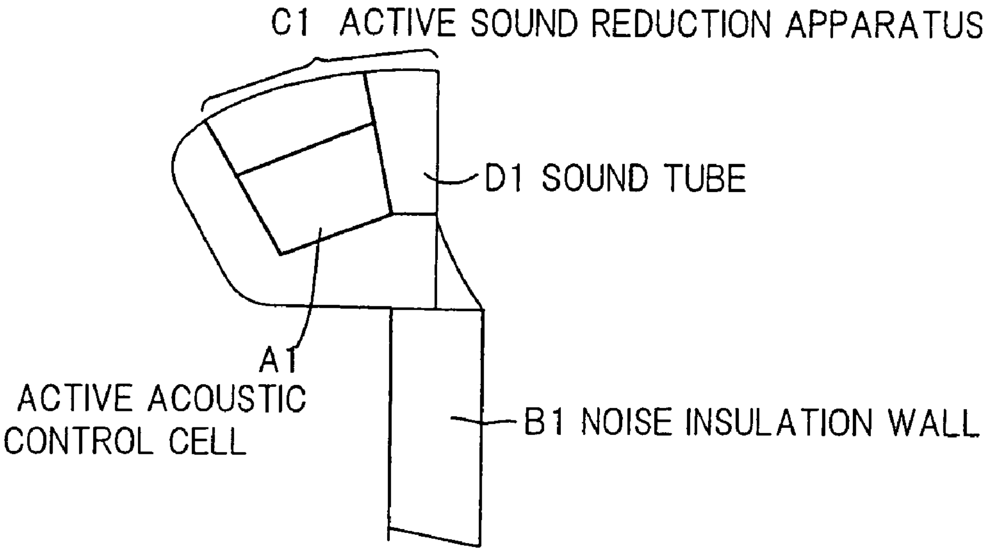
FIGS. 1(*a*) and 1(*b*) are explanation drawings conceptually showing, in a partly extracted form, a first embodiment of the present invention, in which FIG. 1(*a*) shows one sound tube, and FIG. 1(*b*) shows two sound tubes.

Embodiments of the present invention will now be described in detail with reference to the accompanying drawings, but they in no way limit the invention. In the drawings, the same members will be assigned the same numerals, and duplicate explanations will be omitted.

First Embodiment

Figure 1B:
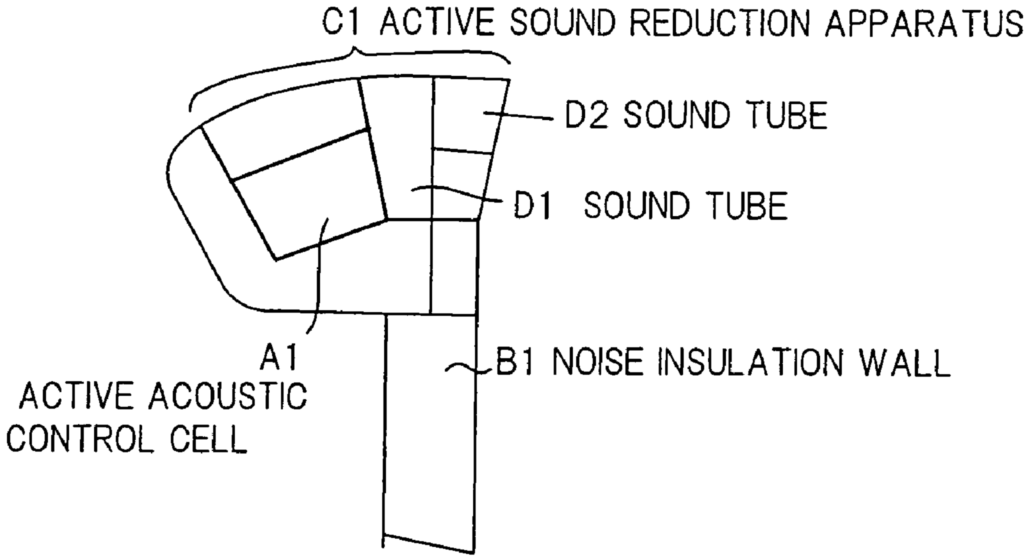
Figure 27:
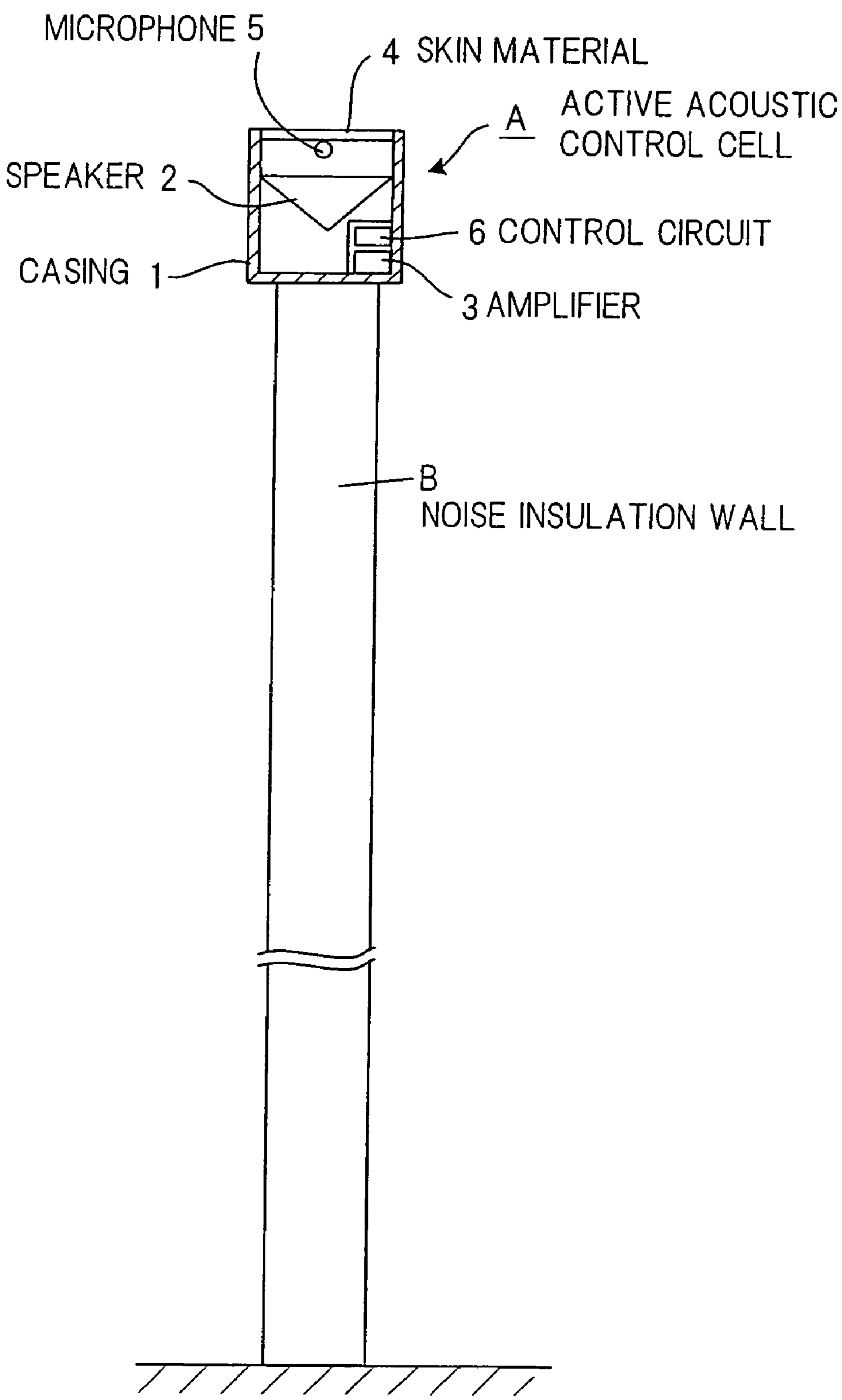
FIG. 27 is an explanation drawing conceptually showing an active noise insulation wall having a row of active acoustic control cells according to an earlier technology.
Figure 28:
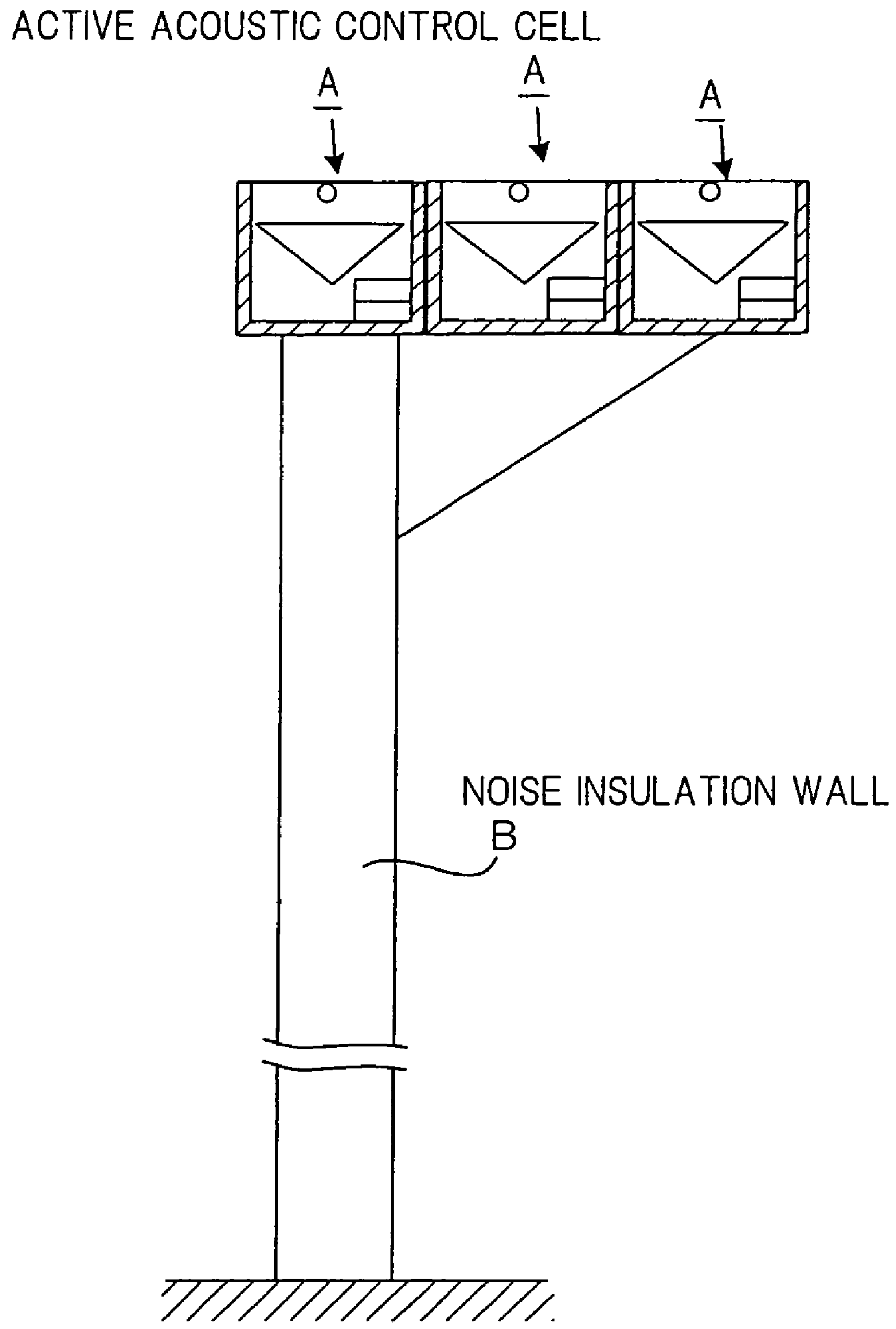
FIG. 28 is an explanation drawing conceptually showing an active noise insulation wall having three rows of the active acoustic control cells according to an earlier technology.

FIGS. 1(*a*) and 1(*b*) are explanation drawings conceptually showing, in a partly extracted form, a first embodiment of the present invention, in which FIG. 1(*a*) shows one sound tube, and FIG. 1(*b*) shows two sound tubes. As shown in both drawings, an active acoustic control cell A1 has the same configuration and function as those of the active acoustic control cell A illustrated in FIG. 27. That is, the active acoustic control cell A1 decreases a diffracted sound pressure component (at the relevant site) of a coming noise by active means. The active acoustic control cell A1 in the present embodiment is combined with a sound tube D1 or sound tubes D1, D2 to constitute a composite active sound reduction apparatus C1. The sound tubes D1 and D2 are different in length. A plurality of the active sound reduction apparatuses C1 are disposed in a row on an upper end surface of a noise insulation wall B1, a vertical wall, along a longitudinal direction of the noise insulation wall B1. The left side in the drawing is a noise source side, e.g., a driveway side, while the right side in the drawing is, for example, a private house side.

The active sound reduction apparatus C1 is constituted by placing the one sound tube D1 or the plurality of sound tubes D1, D2 adjacently to the active acoustic control cell A1 on a side opposite to the source of noise to be reduced. The sound tubes D1, D2 have lengths which are nearly ¼ of wavelengths other than a control target frequency of the active acoustic control cell A1. Thus, the sound tubes D1, D2 reduce noise of a frequency component different from that of the active acoustic control cell A1. FIG. 1(*a*) shows one sound tube, D1, disposed adjacent to the active acoustic control cell A1 on the side opposite to the noise source. Whereas FIG. 1(*b*) shows two sound tubes, D1 and D2, disposed adjacent to the active acoustic control cell A1 on the side opposite to the noise source.

According to the present embodiment, the active acoustic control cell A1 can effectively reduce noise of a specific frequency and a frequency component close to the specific frequency, while the sound tube D1 or the sound tubes D1, D2 can also reduce noises of specific frequencies defined by their lengths, and noises of frequency components close to the specific frequencies. That is, the active acoustic control cell A1 and the sound tube D1 or the sound tubes D1, D2 function compositely in reducing noises, and can effectively reduce noises in a broad frequency region. By restricting the frequency band which the active acoustic control cell is responsible for, the cost can be decreased. The frequency f of a sound wave which can be decreased by the sound tubes D1, D2 is determined by the following equation (rough estimate):

$$f=C/4L \qquad \text{[Equation 1]}$$

where C is the sound velocity (m/s).

Thus, when the length of the sound tube D is 0.16 m, f=531 (Hz). In this case, a sound wave of a frequency of about 531 to 1,000 (Hz) is targeted, and its sound pressure can be decreased.

Second Embodiment

Figure 2:
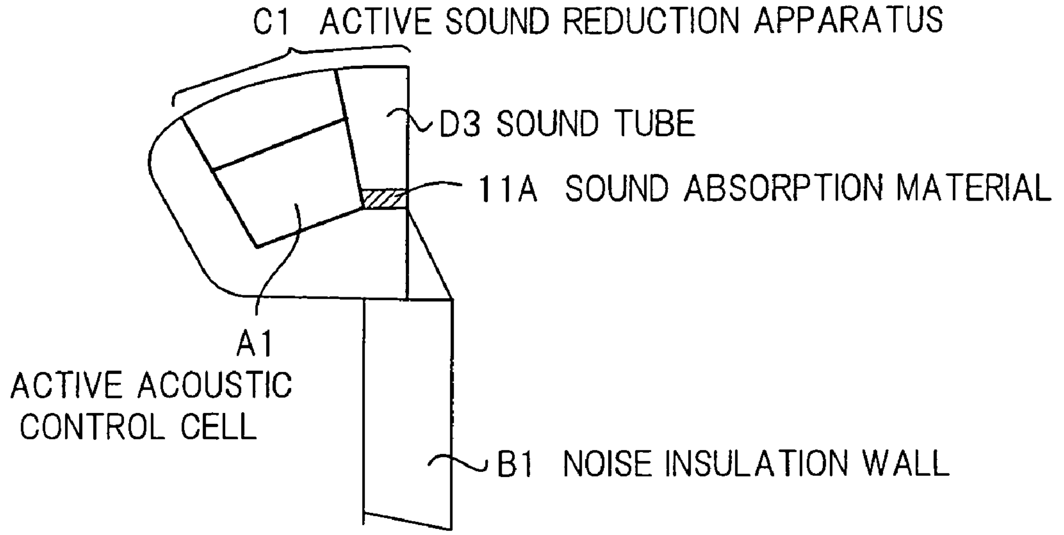
FIG. 2 is an explanation drawing conceptually showing, in a partly extracted form, a second embodiment of the present invention.

FIG. 2 is an explanation drawing conceptually showing, in a partly extracted form, a second embodiment of the present invention. As shown in the drawing, a sound tube D3 of an active sound reduction apparatus C1 in the present embodiment has a structure in which a sound absorption material 11A is disposed at the bottom of the sound tube D1 shown in FIG. 1. This structure is designed to avoid an amplifying effect on a sound wave corresponding to a length which is nearly a half of a wavelength of a sound wave whose sound pressure is decreased by the sound tube D3. That is, the sound absorption material 11A satisfactorily absorbs the above sound wave corresponding to the nearly half length, and a sound wave of a frequency close to the sound wave.

Third Embodiment

Figure 3:
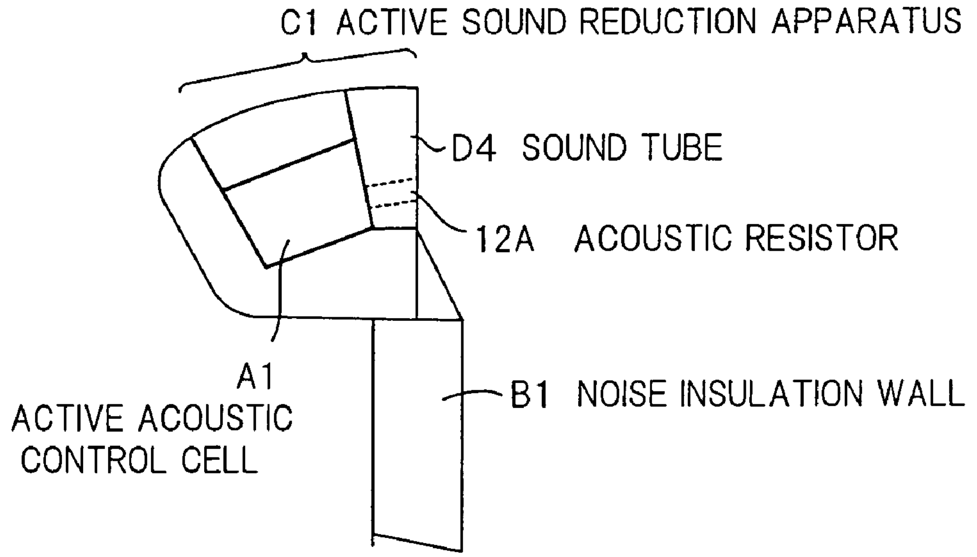
FIG. 3 is an explanation drawing conceptually showing, in a partly extracted form, a third embodiment of the present invention.

FIG. 3 is an explanation drawing conceptually showing, in a partly extracted form, a third embodiment of the present invention. As shown in the drawing, a sound tube D4 of an active sound reduction apparatus C1 in the present embodiment has a structure in which an acoustic resistor 12A, such as a porous plate, is disposed midway through the sound tube D1 illustrated in FIG. 1. This structure is designed to avoid an amplifying effect on a sound wave corresponding to a length which is nearly a half of a wavelength of a sound wave whose sound pressure is decreased by the sound tube D4. That is, the acoustic resistor 12A satisfactorily decreases the above sound wave corresponding to the nearly half length, and a sound wave of a frequency close to the sound wave.

Fourth Embodiment

Figure 4A:
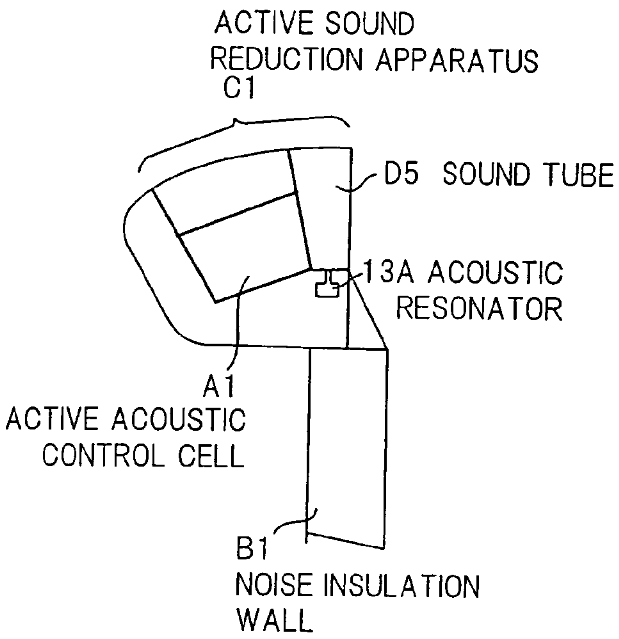
FIGS. 4(*a*) and 4(*b*) are views showing a fourth embodiment of the present invention, in which FIG. 4(*a*) is an explanation drawing conceptually showing the fourth embodiment in a partly extracted form, and FIG. 4(*b*) is an explanation drawing showing an acoustic resonator of the fourth embodiment in an extracted and enlarged form.
Figure 4B:
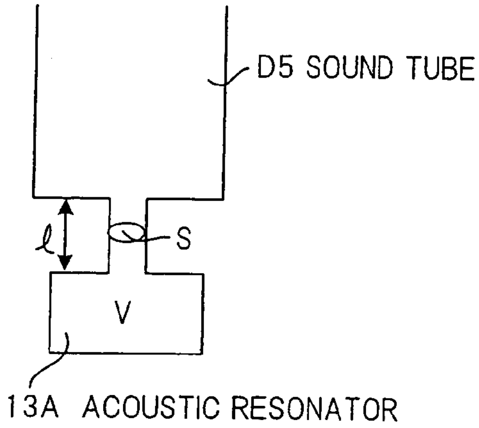

FIG. 4(*a*) is an explanation drawing conceptually showing, in a partly extracted form, a fourth embodiment of the present invention. As shown in the drawing, a sound tube D5 of an active sound reduction apparatus C1 in the present embodiment has a structure in which an acoustic resonator 13A is provided in a form continued from the bottom of the sound tube D1 shown in FIG. 1. This structure is designed to avoid an amplifying effect on a sound wave corresponding to a length which is nearly a half of a wavelength of a sound wave whose sound pressure is decreased by the sound tube D5. That is, the acoustic resonator 13A satisfactorily decreases the sound pressure of the above sound wave corresponding to the nearly half length, and a sound wave of a frequency close to the sound wave.

The frequency f of a sound wave which can be decreased by the acoustic resonator 13A, which is shown as an extracted view in FIG. 4(*b*), is determined by the following equation (rough estimate):

$$f=(C/2\pi)\cdot\sqrt{(S/1)V} \qquad \text{[Equation 2]}$$

where C is the sound velocity (m/s), 1 is the length (m) of a neck portion, S is the cross sectional area ($m^2$) of the neck portion, and V is the volume ($m^3$) of the acoustic resonator.

Fifth Embodiment

Figure 5:
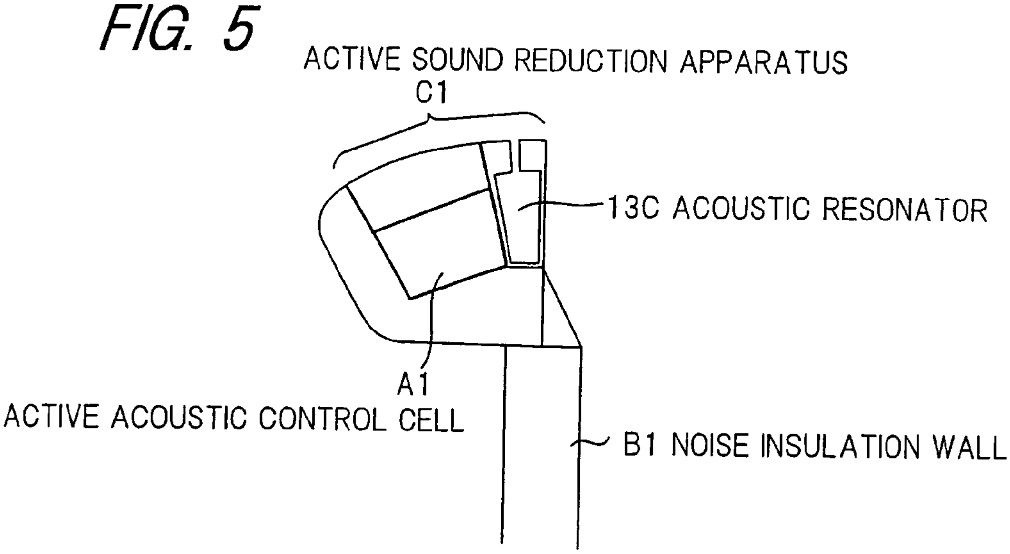
FIG. 5 is an explanation drawing conceptually showing, in a partly extracted form, a fifth embodiment of the present invention.

FIG. 5 is an explanation drawing conceptually showing, in a partly extracted form, a fifth embodiment of the present invention. As shown in the drawing, the present embodiment is a modification of the embodiment illustrated in FIGS. 4(*a*) and 4(*b*), namely, the modification in which the sound tube D5 in the fourth embodiment shown in FIGS. 4(*a*) and 4(*b*) is omitted, and an acoustic resonator 13C is disposed directly on the surface. The acoustic resonator 13C minimizes the sound pressure of a sound wave of a specific frequency at a site near its entrance, thereby decreasing the sound wave of the frequency. Since the acoustic resonator is used, the frequency to be decreased can be controlled arbitrarily even in a limited space. The frequency of the sound wave that can be decreased by the acoustic resonator 13C is determined by the aforementioned Equation 2.

The present embodiment is characterized in that its active sound reduction apparatus can be produced at a low cost, in comparison with a tenth embodiment to be described later on.

In the foregoing first to fifth embodiments, the active sound reduction apparatus C1 having only one active acoustic control cell A1 is used. However, the single active acoustic control cell A1 is not restrictive, and the number of the active acoustic control cells A1 may be two or more.

Embodiments involving two active acoustic control cells will be described as sixth to twelfth embodiments.

Sixth Embodiment

Figure 6:
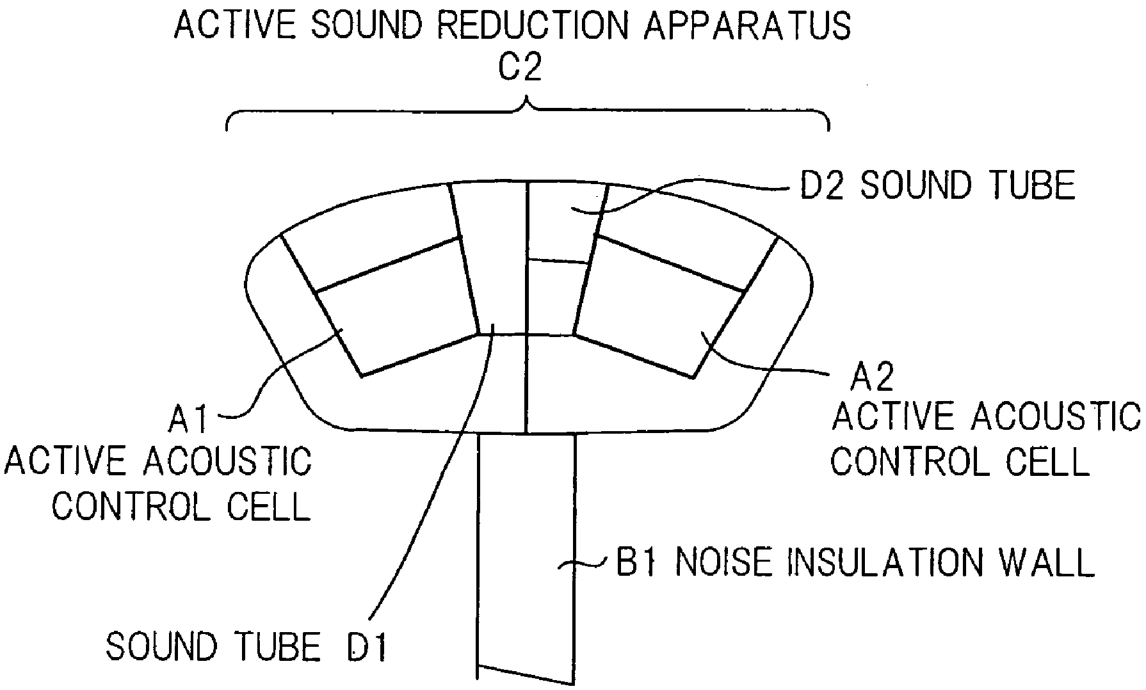
FIG. 6 is an explanation drawing conceptually showing, in a partly extracted form, a sixth embodiment of the present invention.

FIG. 6 is an explanation drawing conceptually showing an active sound reduction apparatus C2 disposed on a noise insulation wall B1, the active sound reduction apparatus C2 having two active acoustic control cells. As shown in the drawing, the active sound reduction apparatus C2 in the present embodiment has the active acoustic control cell A1 illustrated in FIG. 1(*b*), and another active acoustic control cell A2 disposed adjacent to the sound tube D2 on its side opposite to a noise source. The additional active acoustic control cell A2 may be designed to decrease the frequency of a sound wave which is different from those of the active acoustic control cell A1 on the noise source side and the sound tubes D1, D2.

According to the present embodiment, the active acoustic control cells A1, A2 can effectively reduce noises of frequencies specific to them, and noises of frequency components close to the specific frequencies. Furthermore, the sound tubes D1, D2 can reduce noises of specific frequencies defined by their lengths, and noises of frequency components close to the specific frequencies. That is, the active acoustic control cells A1, A2 and the sound tubes D1, D2 exhibit composite functions in reducing noises. Thus, they can effectively reduce noises in a broader frequency region than that in the first embodiment having the single active acoustic control cell A1, and can enhance a noise reducing effect.

Seventh Embodiment

Figure 7:
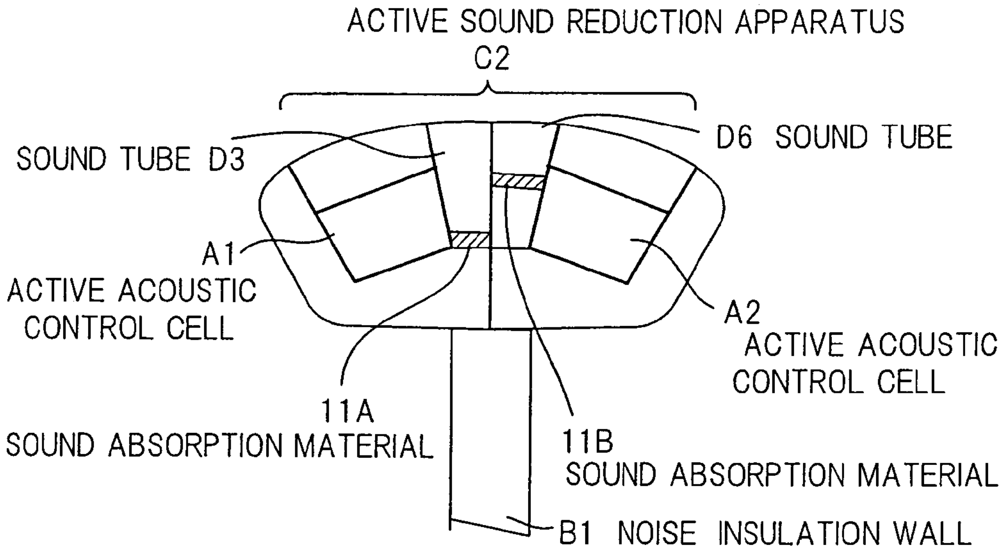
FIG. 7 is an explanation drawing conceptually showing, in a partly extracted form, a seventh embodiment of the present invention.

FIG. 7 is an explanation drawing conceptually showing, in a partly extracted form, a seventh embodiment of the present invention. As shown in the drawing, sound tubes D3, D6 of an active sound reduction apparatus C2 in the present embodiment have structures in which sound absorption materials 11A, 11B are disposed at the bottom of the sound tubes D1, D2 shown in FIG. 6. These structures are designed to avoid an amplifying effect on sound waves corresponding to lengths which are nearly a half of wavelengths of sound waves whose sound pressures are decreased by the sound tubes D3, D6. That is, the sound absorption materials 11A, 11B satisfactorily absorb the above sound waves corresponding to the nearly half lengths, and sound waves of frequencies close to the sound waves.

Eighth Embodiment

Figure 8:
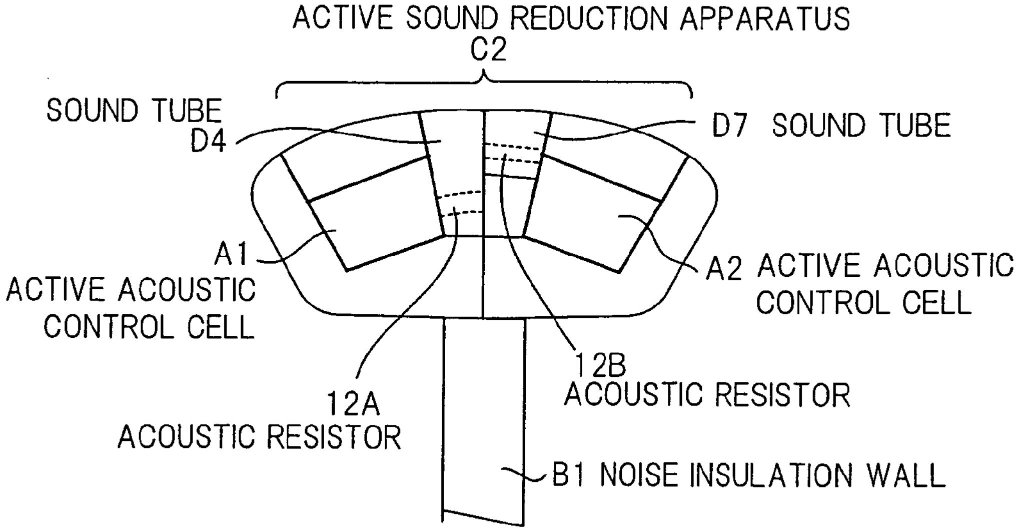
FIG. 8 is an explanation drawing conceptually showing, in a partly extracted form, an eighth embodiment of the present invention.

FIG. 8 is an explanation drawing conceptually showing, in a partly extracted form, an eighth embodiment of the present invention. As shown in the drawing, sound tubes D4, D7 of an active sound reduction apparatus C2 in the present embodiment have structures in which acoustic resistors 12A, 12B, such as porous plates, are disposed midway through the sound tubes D1, D2 shown in FIG. 6. These structures are designed to avoid an amplifying effect on sound waves corresponding to lengths which are nearly a half of wavelengths of sound waves whose sound pressures are decreased by the sound tubes D4, D7. That is, the acoustic resistors 12A, 12B satisfactorily decrease the above sound waves corresponding to the nearly half lengths, and sound waves of frequencies close to the sound waves.

Ninth Embodiment

Figure 9:
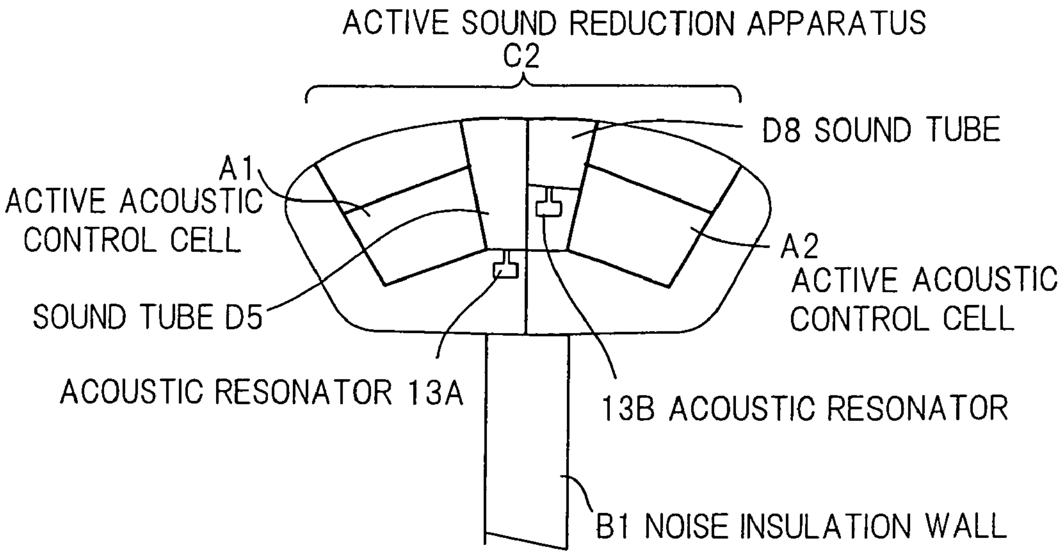
FIG. 9 is an explanation drawing conceptually showing, in a partly extracted form, a ninth embodiment of the present invention.

FIG. 9 is an explanation drawing conceptually showing, in a partly extracted form, a ninth embodiment of the present invention. As shown in the drawing, sound tubes D5, D8 of an active sound reduction apparatus C2 in the present embodiment have structures in which acoustic resonators 13A, 13B are provided in a form continued from the bottom of the sound tubes D1, D2 shown in FIG. 6. These structures are designed to avoid an amplifying effect on sound waves corresponding to lengths which are nearly a half of wavelengths of sound waves whose sound pressures are decreased by the sound tubes D5, D8. That is, the acoustic resonators 13A, 13B satisfactorily decrease the sound pressures of the above sound waves corresponding to the nearly half lengths, and sound waves of frequencies close to these sound waves. The frequency f of the sound wave that can be decreased by the acoustic resonator 13B can also be determined by the same equation as for the acoustic resonator 13A.

Tenth Embodiment

Figure 10:
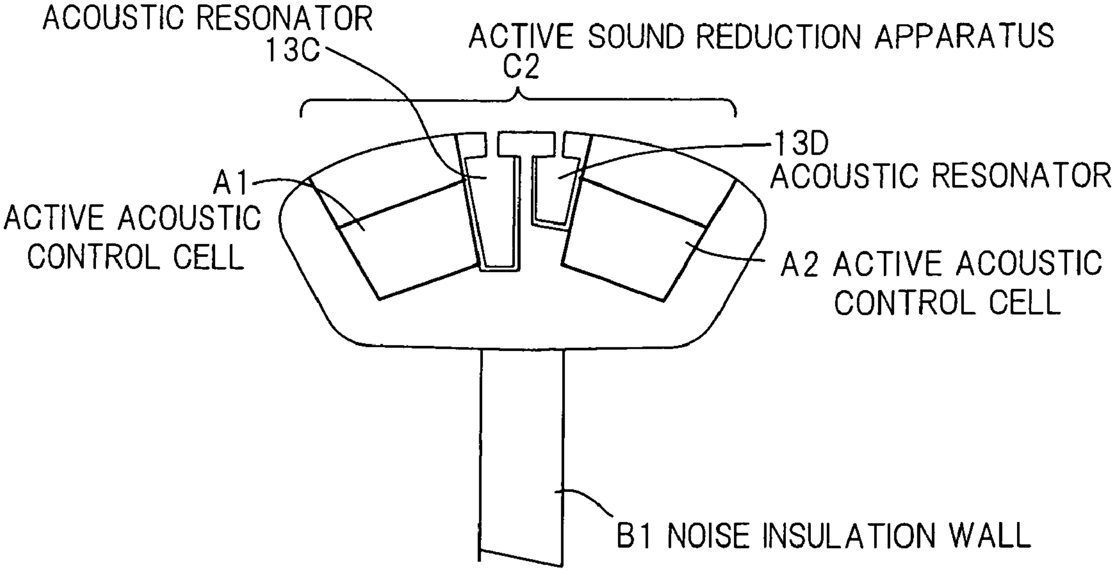
FIG. 10 is an explanation drawing conceptually showing, in a partly extracted form, a tenth embodiment of the present invention.

FIG. 10 is an explanation drawing conceptually showing, in a partly extracted form, a tenth embodiment of the present invention. As shown in the drawing, acoustic resonators 13C, 13D of an active sound reduction apparatus C2 in the present embodiment are directly disposed on the surface of the apparatus. The acoustic resonators 13C, 13D minimize the sound pressures of sound waves of specific frequencies at sites near their entrances, thereby decreasing the sound waves of the frequencies. Since the acoustic resonators are used, the frequencies to be decreased can be controlled arbitrarily even in limited spaces. The frequency f of the sound wave that can be decreased by the acoustic resonator 13D can be determined by the same equation (see Equation 2) as for the acoustic resonator 13C.

According to the present embodiment, noises of two different types of frequencies, other than those which can be decreased by an active sound reduction apparatus, can be reduced in comparison with the fifth embodiment.

Eleventh Embodiment

Figure 11:
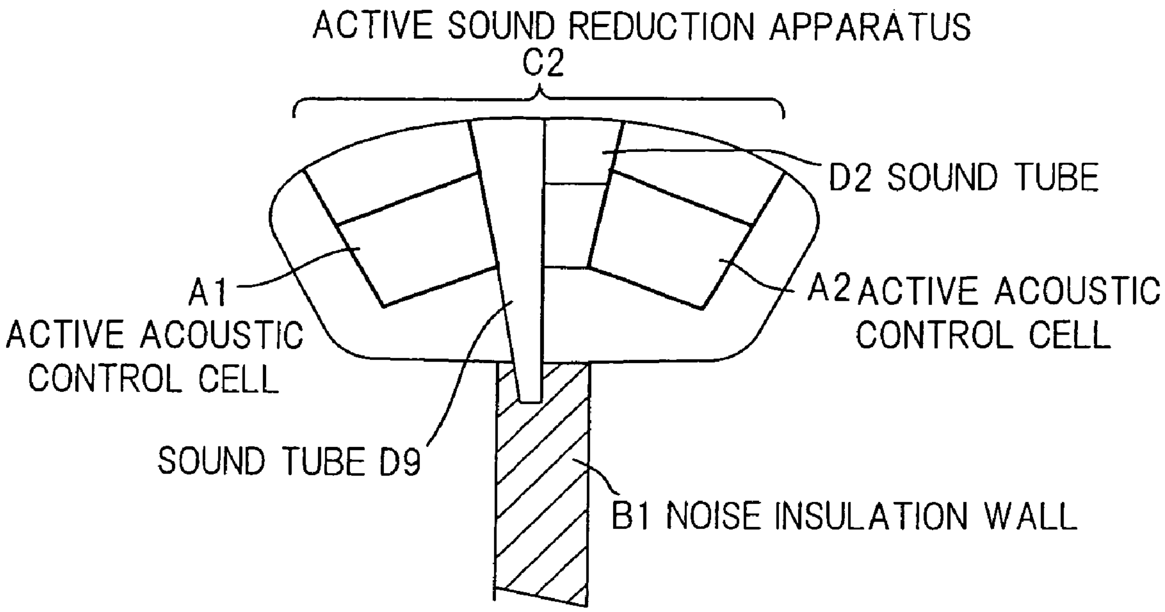
FIG. 11 is an explanation drawing conceptually showing, in a partly extracted form, an eleventh embodiment of the present invention.

FIG. 11 is an explanation drawing conceptually showing, in a partly extracted form, an eleventh embodiment of the present invention. As shown in the drawing, a sound tube D9 of an active sound reduction apparatus C2 in the present embodiment has a bottom portion buried in a depression formed in an upper surface of a noise insulation wall B1. The length of the sound tube D9 is determined by the wavelength of a sound wave which is decreased by this sound tube, as stated above. Thus, the lower the frequency of a sound wave to be decreased, the longer the sound tube D9 is. By burying the bottom portion of the sound tube D9 in the depression formed in the upper surface of the noise insulation wall B1, the entire bulk can be decreased.

Twelfth Embodiment

Figure 12:
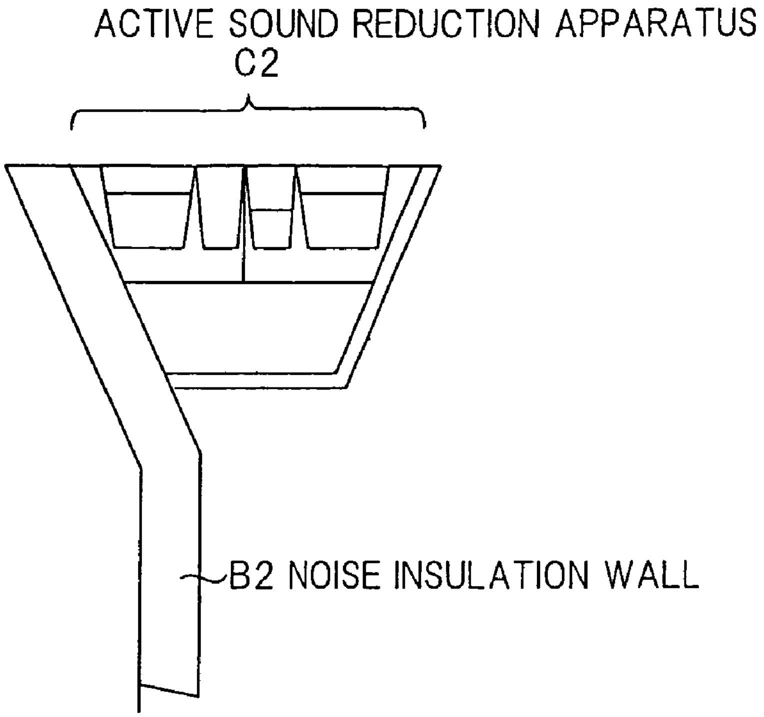
FIG. 12 is an explanation drawing conceptually showing, in a partly extracted form, a twelfth embodiment of the present invention.

FIG. 12 is an explanation drawing conceptually showing, in a partly extracted form, a twelfth embodiment of the present invention. As shown in the drawing, the present embodiment is an embodiment in which the shape of a noise insulation wall having an active sound reduction apparatus C2 disposed thereon is different. As shown in the drawing, a noise insulation wall B2 has an upper portion inclined toward a noise source (leftward in the drawing). The active sound reduction apparatus C2 is mounted on the noise insulation wall B2 with the use of this inclined surface. A sound absorption material may be disposed on a side surface of the noise insulation wall B2 on the noise source side.

Thirteenth Embodiment

Figure 13:
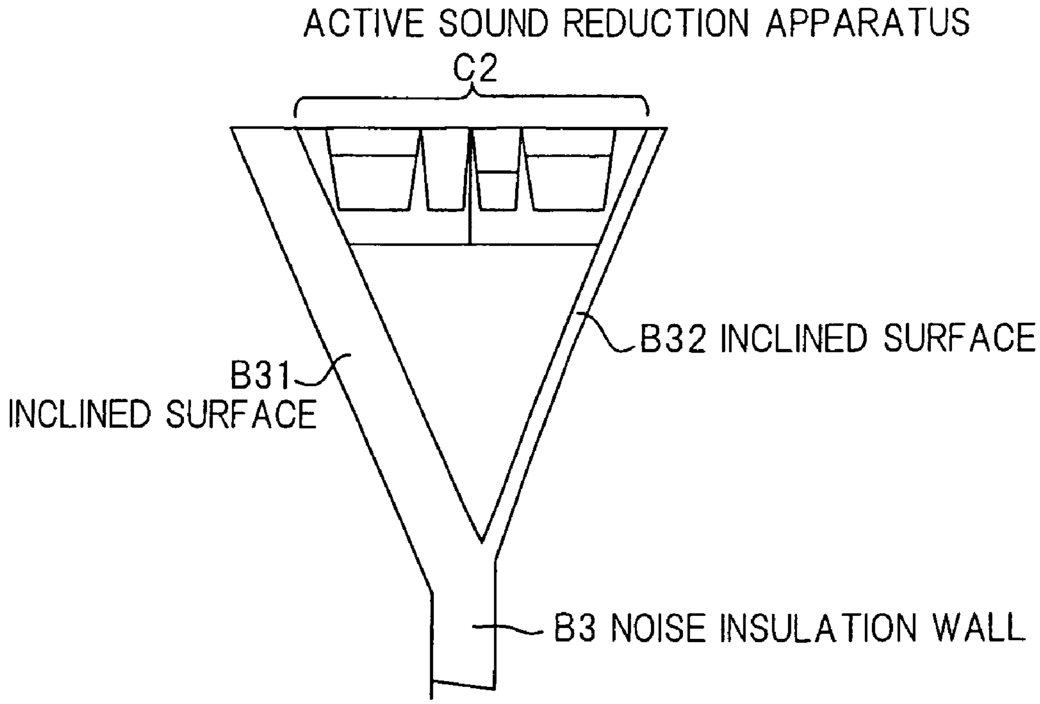
FIG. 13 is an explanation drawing conceptually showing, in a partly extracted form, a thirteenth embodiment of the present invention.

FIG. 13 is an explanation drawing conceptually showing, in a partly extracted form, a thirteenth embodiment of the present invention. As shown in the drawing, the present embodiment is an embodiment in which the shape of a noise insulation wall having an active sound reduction apparatus C2 disposed thereon is different. As shown in the drawing, a noise insulation wall B3 has an upper portion branched to form an inclined surface B31 inclined toward a noise source (leftward in the drawing) and an inclined surface B32 inclined toward a side opposite to the noise source side. The active sound reduction apparatus C2 is disposed between both inclined surfaces B31 and B32. A sound absorption material may be disposed on a side surface of the noise insulation wall B3 on the noise source side.

Fourteenth Embodiment

Figure 14:
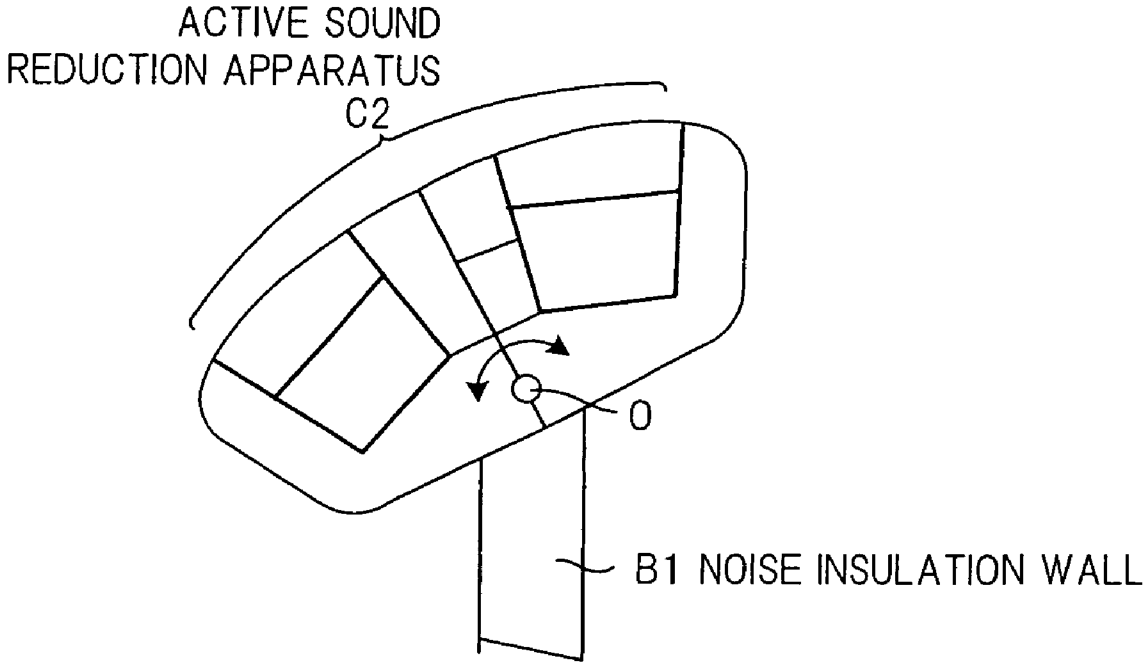
FIG. 14 is an explanation drawing conceptually showing, in a partly extracted form, a fourteenth embodiment of the present invention.

FIG. 14 is an explanation drawing conceptually showing, in a partly extracted form, a fourteenth embodiment of the present invention. As shown in the drawing, according to the present embodiment, the whole of an active sound reduction apparatus C2 is tiltable about a turn portion O as a turn center.

According to the present embodiment, a noise insulation region can be adjusted, because the shape and the angle of inclination of the active sound reduction apparatus C2 determine a region in which the sound pressure of a diffracted wave can be decreased by the active sound reduction apparatus C2.

The active sound reduction apparatuses used in the active noise insulation walls according to the foregoing first to fourteenth embodiments need not be limited to the active sound reduction apparatuses C1, C2. Generally, the active sound reduction apparatus can be constituted by disposing one sound tube or a plurality of sound tubes adjacent to the active acoustic control cell on its side facing a noise source as a target of sound reduction (e.g., a driveway side), or on its side opposite to the noise source, or on both of the noise source side and the opposite side of the active acoustic control cell. The number of the active acoustic control cells need not be restricted to one or two, and the active sound reduction apparatus having various combinations of the active acoustic control cells can be constituted. Each sound tube in each active sound reduction apparatus has a length which is nearly ¼ of a wavelength of a sound wave other than a control target frequency for the active acoustic control cell. Thus, the sound tube can reduce noise of a frequency component which is different from the target frequency for the active acoustic control cell.

Figure 15A:
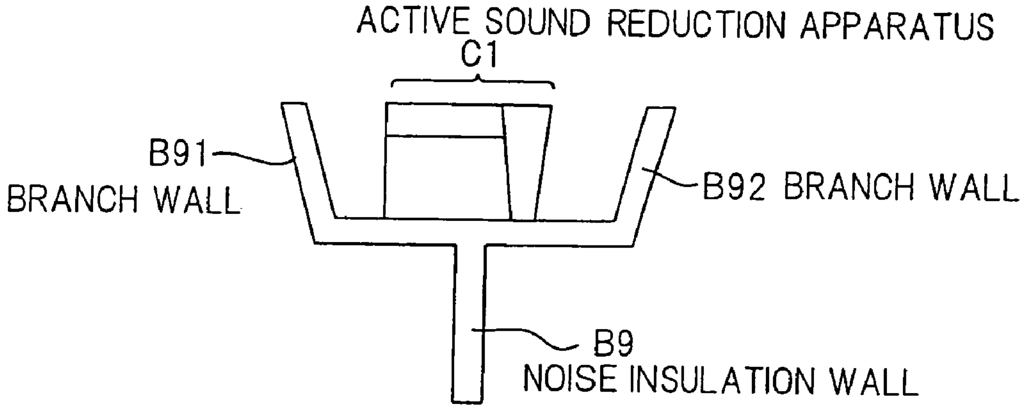
FIGS. 15(*a*) and 15(*b*) are explanation drawings conceptually showing modifications of the structure of a noise insulation wall in an active noise insulation wall according to the present invention.
Figure 15B:
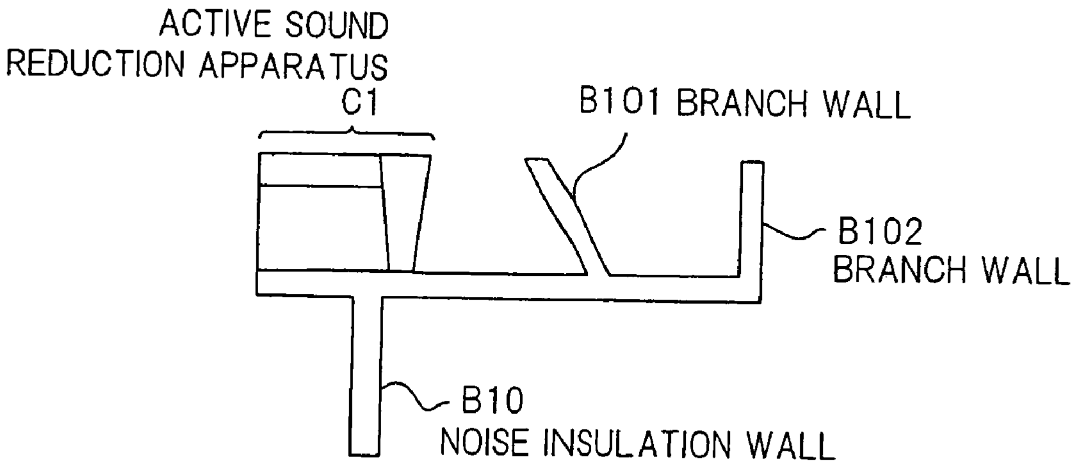

Similarly, there is no restriction on the structure of the noise insulation walls used in the active noise insulation walls according to the first to fourteenth embodiments, namely, the structure of the noise insulation walls combined with the active sound reduction apparatuses. For example, the structure may be a structure as shown in FIG. 15(*a*) or 15(*b*). A noise insulation wall B9 shown in FIG. 15(*a*) has an upper end portion bifurcating to form branch walls B91 and B92 extending upward. An active sound reduction apparatus C1 is disposed between the branch walls B91 and B92. There may be only one branch wall, B91 or B92, on one side. Alternatively, there may be three or more of the branch walls B91 or B92. A noise insulation wall B10 shown in FIG. 15(*b*), like the noise insulation wall B9, has an upper end portion bifurcating to form branch walls B101 and B102 extending upward. However, the branch walls B101 and B102 are both formed on a side opposite to a noise source (of course, may be on a noise source side) relative to an active sound reduction apparatus C1. The number of the branch walls, B101, B102, is undoubtedly not restricted to two. When the active sound reduction apparatus is combined with the noise insulation wall B9 or B10 as shown in FIG. 15(*a*) or 15(*b*), the sound reducing function at the branch walls B91, B92 or B101, B102 is added, so that more effective noise insulation can be performed.

According to the first to fourteenth embodiments, the active sound reduction apparatuses C1 or C2 are disposed only in one row on the noise insulation wall. However, a plurality of edges may be formed above the noise insulation wall, and only the active acoustic control cells A, or the active sound reduction apparatuses C1 or active sound reduction apparatuses C2 may be disposed in a plurality of rows. Embodiments in which only the active acoustic control cells A, or the active sound reduction apparatuses C1 or active sound reduction apparatuses C2 are disposed in a plurality of rows will be described as fifteenth to eighteenth embodiments.

Fifteenth Embodiment

Figure 16:
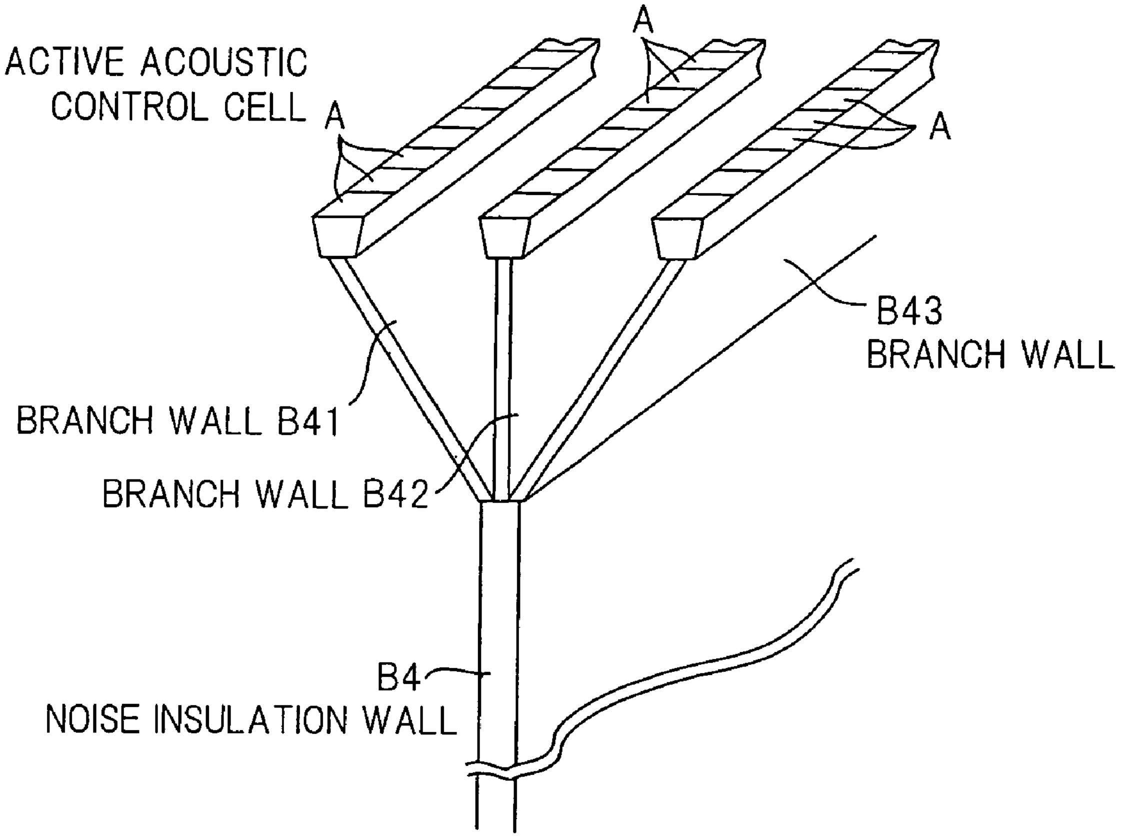
FIG. 16 is an explanation drawing conceptually showing, in a partly extracted form, a fifteenth embodiment of the present invention.

FIG. 16 is an explanation drawing conceptually showing, in a partly extracted form, a fifteenth embodiment of the present invention. As shown in the drawing, a sound insulation wall B4 according to the present embodiment has three branch walls B41, B42 and B43 extending upward from an upper end of a vertical wall, and rows made by arranging a plurality of active acoustic control cells A are formed on the upper end surfaces of the branch walls B41, B42 and B43. The respective rows of the active acoustic control cells A are disposed with predetermined spacing between the adjacent rows. It is not absolutely necessary to make the characteristics, size, etc. of the acoustic control cells A the same, and their characteristics and sizes may be freely combined. Moreover, the three branch walls B41, B42 and B43 in the present embodiment may have upper surfaces different in height position. That is, there is no restriction on the height positions of their upper surfaces.

When the active acoustic control cells A are thus arranged in plural rows with spacing between the rows, the cost of the active noise insulation wall can be decreased, without a marked deterioration of the sound reducing effect, in comparison with the active acoustic control cells A being arranged without spacing between the adjacent rows. That is, the inventors of the present invention have found that the sound reducing effect is greater when the active acoustic control cells A are arranged in rows with spacing between the rows in a direction perpendicular to a longitudinal direction of the noise insulation wall B, than when the active acoustic control cells A are arranged in rows adjacently without spacing between the rows. The present embodiment is based on this finding. Providing the plural rows with predetermined spacing can obtain a more satisfactory sound reducing effect than providing the plural rows contiguously (i.e. adjacently with no spacing). At the same time, the number of the active acoustic control cells can be decreased, compared with the disposition of the active acoustic control cells such that all of the adjacent spaces are filled with the active acoustic control cells. Thus, the spaced provision of the plural rows can contribute to a decreased cost.

Sixteenth Embodiment

Figure 17:
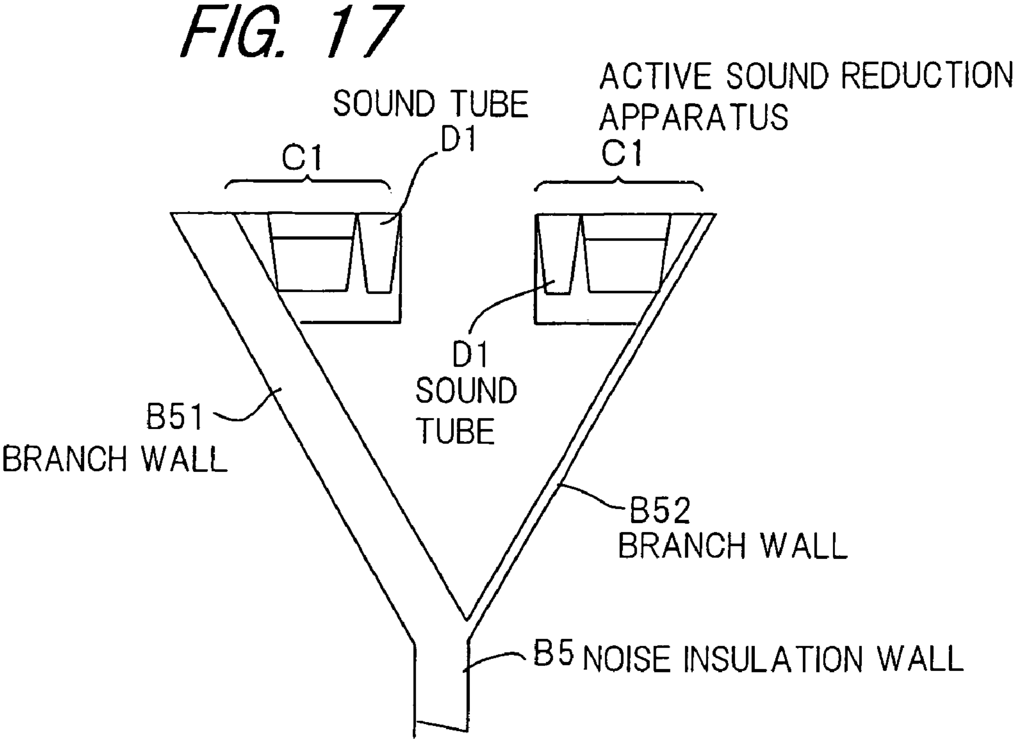
FIG. 17 is an explanation drawing conceptually showing, in a partly extracted form, a sixteenth embodiment of the present invention.

FIG. 17 is an explanation drawing conceptually showing, in a partly extracted form, a sixteenth embodiment of the present invention. As shown in the drawing, the present embodiment is a modification of the thirteenth embodiment shown in FIG. 13. A noise insulation wall B5 has two branch walls B51 and B52 extending upward from an upper end of a vertical wall, and two active sound reduction apparatuses C1 are disposed with spacing on both branch walls B51 and B52 of the noise insulation wall B5. In this case, there is also a spacing between sound tubes constituting a portion of the active sound reduction apparatuses C1. If the sound tubes have the same depth, a better sound reducing effect can be obtained for a frequency component to be decreased by the sound tube, than when the active sound reduction apparatuses C1 are placed contiguously. As the wavelength of a sound wave to be decreased lengthens, a greater spacing between the active sound reduction apparatuses C1 proves more effective.

The present embodiment involves a replacement of the active acoustic control cells A by the active sound reduction apparatuses C1. Thus, a more satisfactory sound reducing effect can be obtained than when plural rows of the active sound reduction apparatuses C1 are disposed contiguously without spacing between the adjacent rows. At the same time, the number of the active sound reduction apparatuses can be decreased, compared with the disposition of the active sound reduction apparatuses such that all of the adjacent spaces are filled with the active sound reduction apparatuses. Thus, the spaced provision of the plural rows can contribute to a decreased cost.

Seventeenth Embodiment

Figure 18:
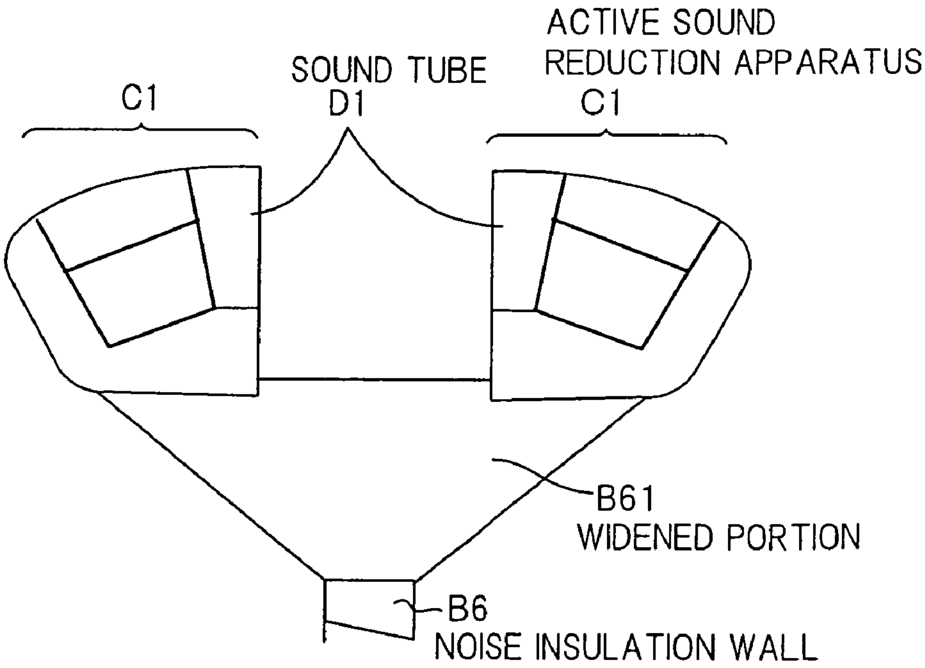
FIG. 18 is an explanation drawing conceptually showing, in a partly extracted form, a seventeenth embodiment of the present invention.

FIG. 18 is an explanation drawing conceptually showing, in a partly extracted form, a seventeenth embodiment of the present invention. As shown in the drawing, the present embodiment is a modification of the sixteenth embodiment shown in FIG. 17. A noise insulation wall B6 has a widened portion B61 in an upper end portion thereof, the widened portion B61 expanding in a direction perpendicular to the longitudinal direction of the noise insulation wall B6. Two active sound reduction apparatuses C1 are disposed with spacing on the widened portion B61. The active sound reduction apparatus C1 is movable on the widened portion B61, so that the distance between the active sound reduction apparatuses C1 can be freely adjusted.

The present embodiment also functions like the sixteenth embodiment. According to the present embodiment, moreover, the position of the active sound reduction apparatus C1 on the widened portion B61 can be adjusted. Thus, such a distance between both active sound reduction apparatuses C1 as will obtain optimal sound reducing effect can be easily secured. Furthermore, the area occupied in an installation place on a road or the like can be easily adjusted. Depending on a highway or an ordinary road, there may be a restriction on an installation area where the active noise insulation wall can be used.

Eighteenth Embodiment

Figure 19:
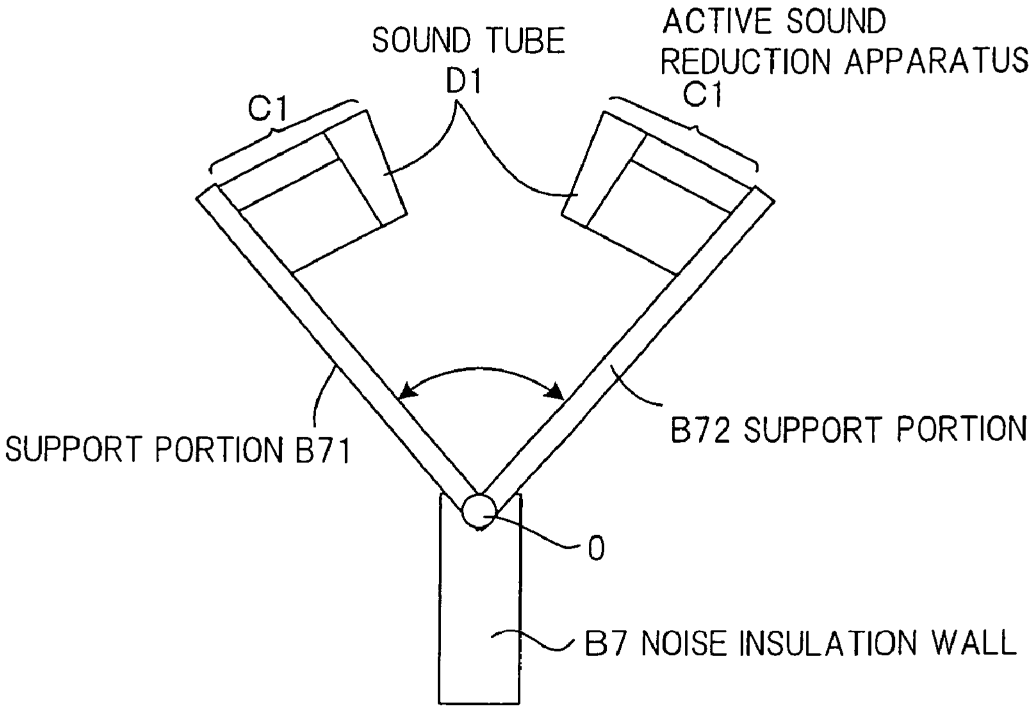
FIG. 19 is an explanation drawing conceptually showing, in a partly extracted form, an eighteenth embodiment of the present invention.

FIG. 19 is an explanation drawing conceptually showing, in a partly extracted form, an eighteenth embodiment of the present invention. As shown in the drawing, the present embodiment is a modification of the sixteenth embodiment shown in FIG. 17. A noise insulation wall B7 has support portions B71, B72 in an upper end portion thereof, the support portions B71, B72 having base ends supported by a turn portion O so as to be rotatable normally and reversely. Active sound reduction apparatuses C1 are mounted on the support portions B71 and B72. Thus, both active sound reduction apparatuses C1 integrally rotate in accordance with the normal or reverse rotation of the support portions B71, B72, so that the distance between them can be increased or decreased. The active sound reduction apparatuses C1 may be provided with separate turn portions, and mounted to the support portions B71 and B72 so as to be normally or reversely rotatable. In this case, when the support portions B71, B72 open or close upon their normal or reverse rotation, the angle of installation of the active sound reduction apparatus C1 relative to the installation surface (ground surface) can be independently adjusted to a preferred angle, such as a constant angle.

The present embodiment also functions like the sixteenth embodiment. According to the present embodiment, moreover, the distance between the active sound reduction apparatuses C1 can be easily adjusted by rotating the support portions B71, B72 normally or reversely. Thus, such a distance between both active sound reduction apparatuses C1 as will obtain optimal sound reducing effect can be easily secured. Furthermore, the area occupied in an installation place on a road or the like can be easily adjusted. Depending on a highway or an ordinary road, there may be a restriction on an installation area where the active noise insulation wall can be used.

The active sound reduction apparatuses used in the active noise insulation walls according to the fifteenth to eighteenth embodiments may be any of the active sound reduction apparatuses usable in the first to fourteenth embodiments. The difference exists only in that the fifteenth to eighteenth embodiments have plural rows of active acoustic control cells or active sound reduction apparatuses with spacing between the adjacent rows, while the first to fourteenth embodiments have a single row of active sound reduction apparatuses. Therefore, active sound reduction apparatuses of different types may, of course, be disposed in respective rows.

Figure 20:
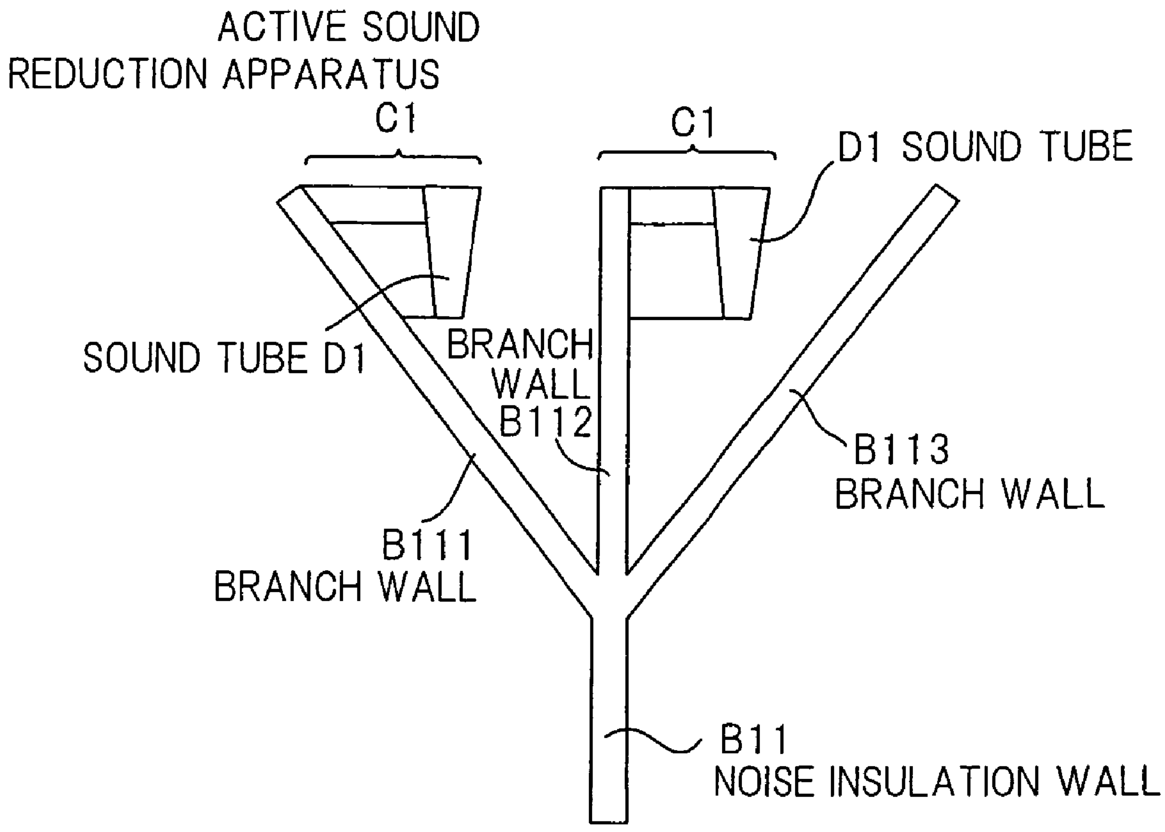
FIG. 20 is an explanation drawing conceptually showing a modification of the structure of a noise insulation wall in an active noise insulation wall according to the present invention.

Similarly, there is no restriction on the structure of the noise insulation walls used in the active noise insulation walls according to the fifteenth to eighteenth embodiments, i.e., the noise insulation walls combined with the active sound reduction apparatuses. For example, a structure as shown in FIG. 20 is acceptable. A noise insulation wall B11 shown in FIG. 20 has an upper end portion trifurcating to form branch walls B111, B112 and B113 extending upward. An active sound reduction apparatus C1 is disposed on each of the branch walls B111 and B112, as in the embodiment shown in FIG. 17. On the other hand, no active sound reduction apparatus C1 is disposed on the branch wall B113. As noted from this, there is no need to dispose the active sound reduction apparatuses C1 on all edges of the noise insulation wall B11, and the branch wall B113 acting as a mere noise insulation wall may be provided. It goes without saying that there are no restrictions on the number of the branch walls B113 functioning merely as noise insulation walls, or on the position of the branch wall B113 relative to the other branch walls B111 and B112.

In the embodiments shown in FIGS. 17 to 20, the sound tubes of the active sound reduction apparatuses C1 were all the sound tubes D1, but they are not limited to the sound tubes D1. The sound tubes can be selected arbitrarily depending on the frequency to be decreased. For example, the active sound reduction apparatus may be formed of only the active sound reduction apparatus C1 having the sound tube D2. Alternatively, one of the right and left active sound reduction apparatuses C1 may be formed of the active sound reduction apparatus C1 having the sound tube D1, and the other active sound reduction apparatus C1 may be formed of the active sound reduction apparatus C1 having the sound tube D2. Of importance is that the active sound reduction apparatuses C1 having various sound tubes may be combined as desired.

In recent years, tall buildings are often constructed near a noise source, such as a highway. In this case, it may be necessary to reduce noise traveling rectilinearly from the noise source past the upper edge of the noise insulation wall B, namely, noise diffusing obliquely upwardly of the noise insulation wall B. This demand can be met if means for reducing noise traveling rectilinearly from the noise source past the upper edge of the noise insulation wall B is provided on one of the plural edges in the embodiments shown in FIGS. 16 to 20. Thus, the following nineteenth and twentieth embodiments are proposed.

Nineteenth Embodiment

Figure 21:
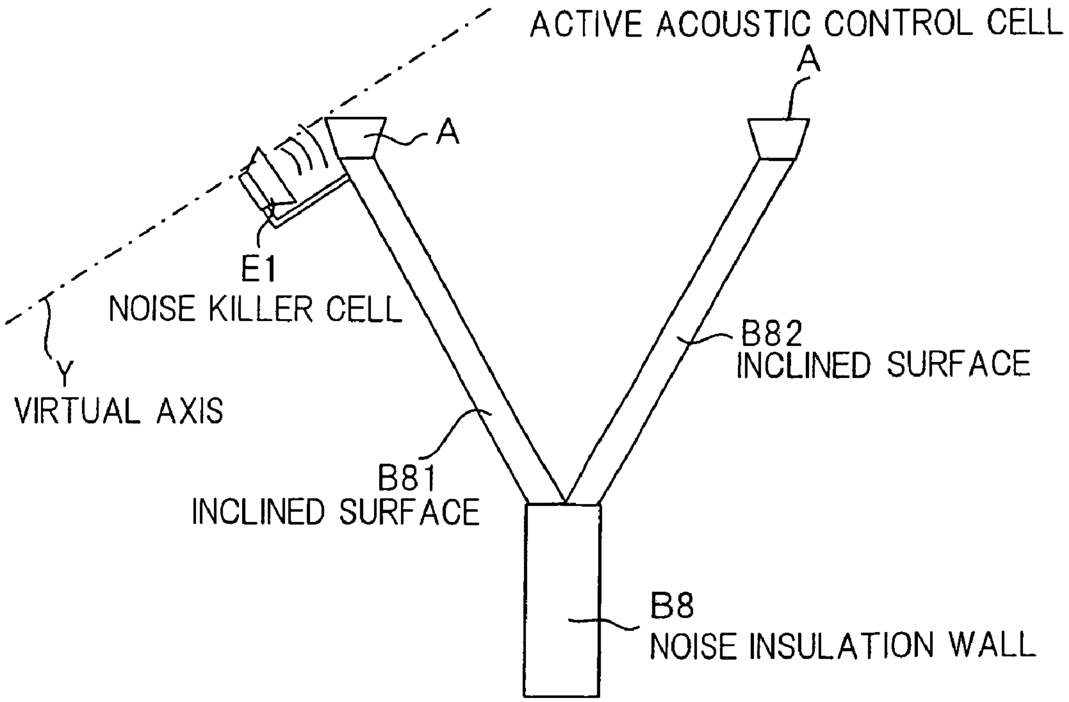
FIG. 21 is an explanation drawing conceptually showing, in a partly extracted form, a nineteenth embodiment of the present invention.

FIG. 21 is an explanation drawing conceptually showing, in a partly extracted form, a nineteenth embodiment of the present invention. As shown in the drawing, the present embodiment is a modification of the fifteenth embodiment shown in FIG. 16. A noise insulation wall B8 has an upper end portion branching to form an inclined surface B81 inclined toward a noise source side (left side in the drawing), and an inclined surface B82 inclined toward a side opposite to the noise source side. Active acoustic control cells A are disposed on the upper end surfaces of the inclined surfaces B81 and B82 of the noise insulation wall B8. Simultaneously, a noise killer cell E1 is provided on the inclined surface B81 to reduce noise traveling rectilinearly from the noise source past the end of the active acoustic control cell A on the inclined surface B81 (the upper end of the active noise insulation wall) (i.e., noise running along a virtual axis Y indicated by a one-dot chain line in FIG. 21).

Figure 22:
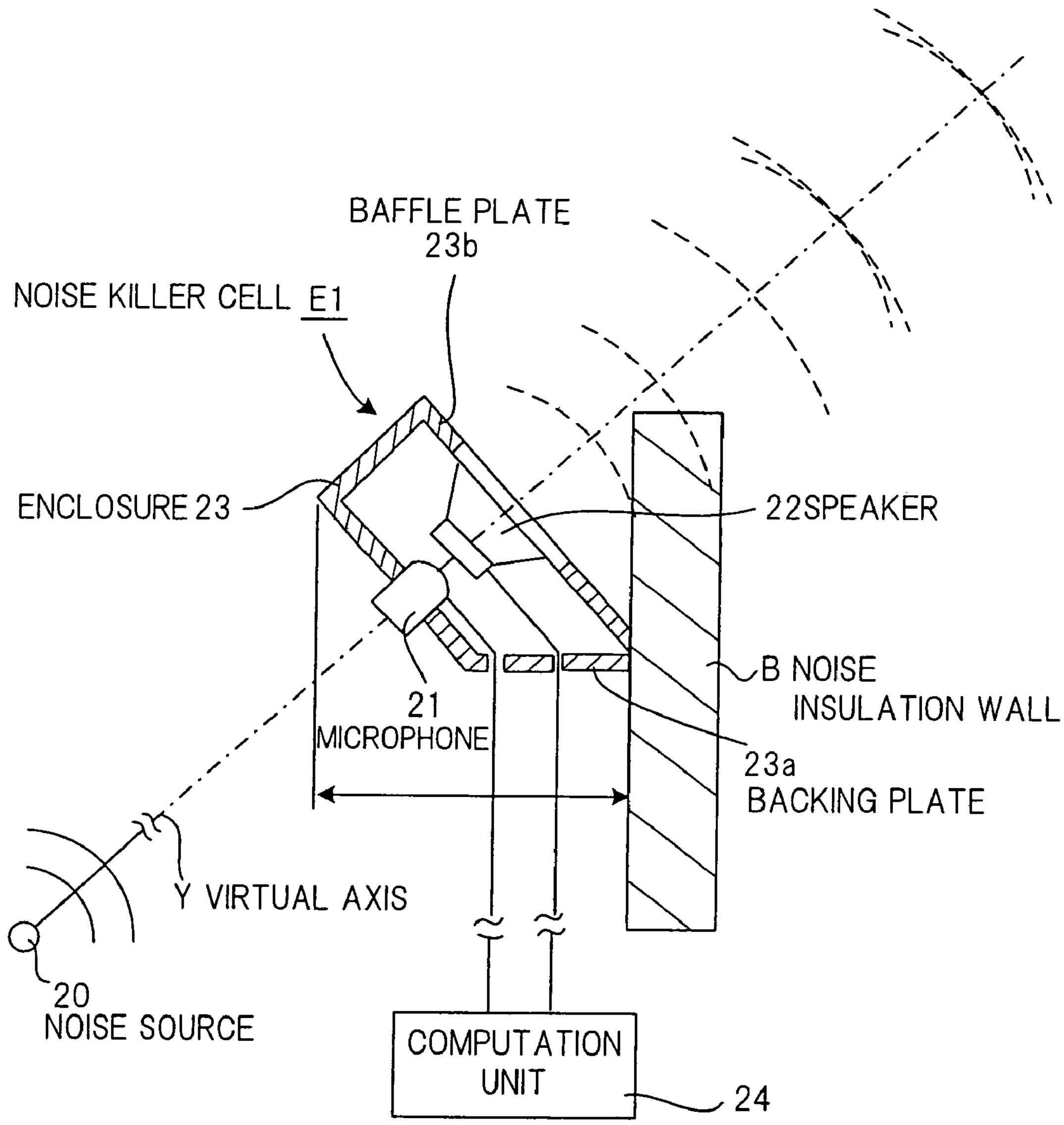
FIG. 22 is an explanation drawing conceptually showing an example of a noise killer cell used in the embodiment illustrated in FIG. 21.

FIG. 22 is an explanation drawing conceptually showing the noise killer cell E1 in a partly extracted form. As shown in the drawing, the noise killer cell E1 has a microphone 21 and a speaker 22 placed on the virtual axis Y connecting a noise source 20 and the upper end portion of the noise insulation wall B. The microphone 21 detects noise emitted from the noise source 20, while the speaker 22 emits a noise killer sound in a direction opposite to the direction of the noise source 20. The microphone 21 and the speaker 22 are housed in an enclosure 23 and mounted on the noise insulation wall B via the enclosure 23. That is, a side of the enclosure 23 facing the noise source 20 is covered with a backing plate 23*a*, while a side of the enclosure 23 opposite to the noise source 20 is open for issuing a noise killer sound produced by the speaker 22. The speaker 22 is attached to a baffle plate 23*b*, and housed in the enclosure 23. The microphone 21 is attached to nearly the center of the backing plate 23*a*. An output of the microphone 21 is fed to a computation unit 24, which performs a predetermined computation to feed an output signal to the speaker 22.

Figure 23:
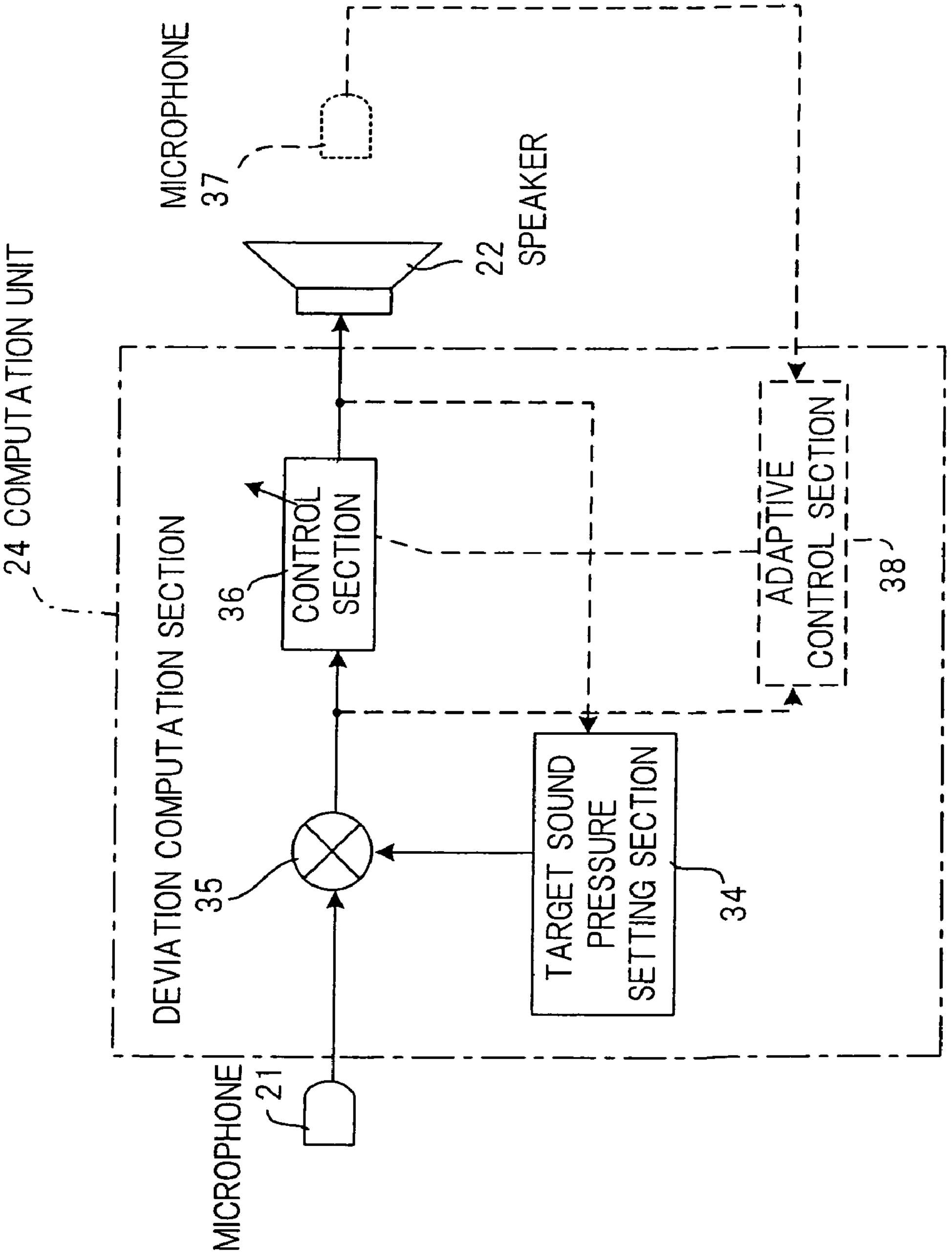
FIG. 23 is a block diagram showing the configuration of the noise killer cell illustrated in FIG. 22.

FIG. 23 is a block diagram of the noise killer cell E1. As shown in the drawing, the computation unit 24 is basically composed of a deviation computation section 35 for computing a deviation between a voltage proportional to a sound pressure, an output signal of a target sound pressure setting section 34 for generating a voltage proportional to a target sound pressure (normally, nearly zero), and a voltage proportional to noise detected by the microphone 21; and a control section 36 for generating a noise killer sound, which has a sound pressure identical with and a phase opposite to, the sound pressure and phase of noise at certain points on a line segment connecting the noise insulation wall B and the speaker 22, based on the deviation computed by the deviation computation section 35. The noise killer sound is emitted by the speaker 22. As a result, a synthesis sound combined from the noise and the noise killer sound has a sound pressure, at the certain points on the line segment connecting the upper end portion of the noise insulation wall B and the speaker 22, of nearly zero. Thus, propagation of the noise from such points to the outside can be prevented. For more effective muffling, a sound pressure in a region to be actually muffled may be detected by another microphone 37 for monitoring, and a control parameter of the control section 36 may be computed by a separately provided adaptive control section 38 based on the sound pressure in the region to be actually muffled and the deviation computed by the deviation computation section 35. In this case, the output of the control section 36 is fed back to the target sound pressure setting section 34 to adjust the target sound pressure.

According to the nineteenth embodiment, therefore, the active acoustic control cells A disposed in two rows can reduce noise leaking to areas below the noise insulation wall B8, namely, a diffracted sound, and the noise killer cells E1 can reduce noise diffusing to areas above the noise insulation wall B8, namely, a rectilinearly traveling sound. Consequently, satisfactory noise reduction can be achieved in a wide range, including areas above the noise insulation wall B8.

Twentieth Embodiment

Figure 24:
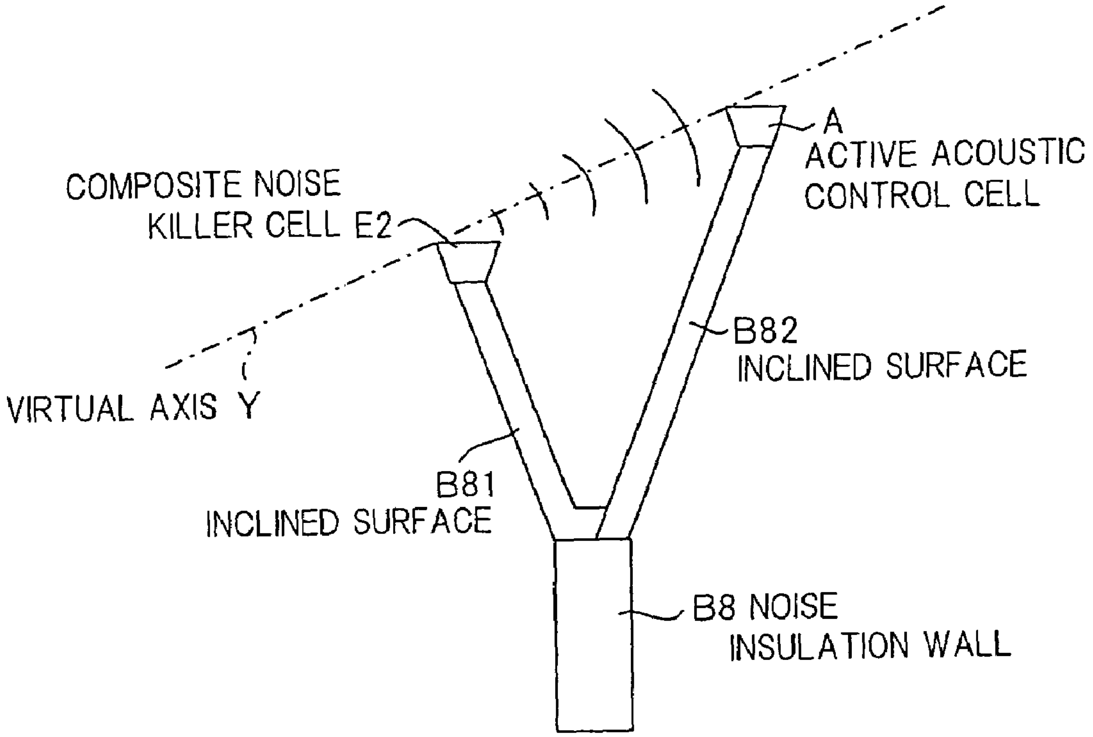
FIG. 24 is an explanation drawing conceptually showing, in a partly extracted form, a twentieth embodiment of the present invention.

FIG. 24 is an explanation drawing conceptually showing, in a partly extracted form, a twentieth embodiment of the present invention. As shown in the drawing, the present embodiment is a modification of the nineteenth embodiment shown in FIG. 21. That is, a composite noise killer cell E2 is disposed instead of the active acoustic control cell A of the embodiment shown in FIG. 21. The composite noise killer cell E2 has the functions of the active acoustic control cell A and the noise killer cell E1.

Figure 25:
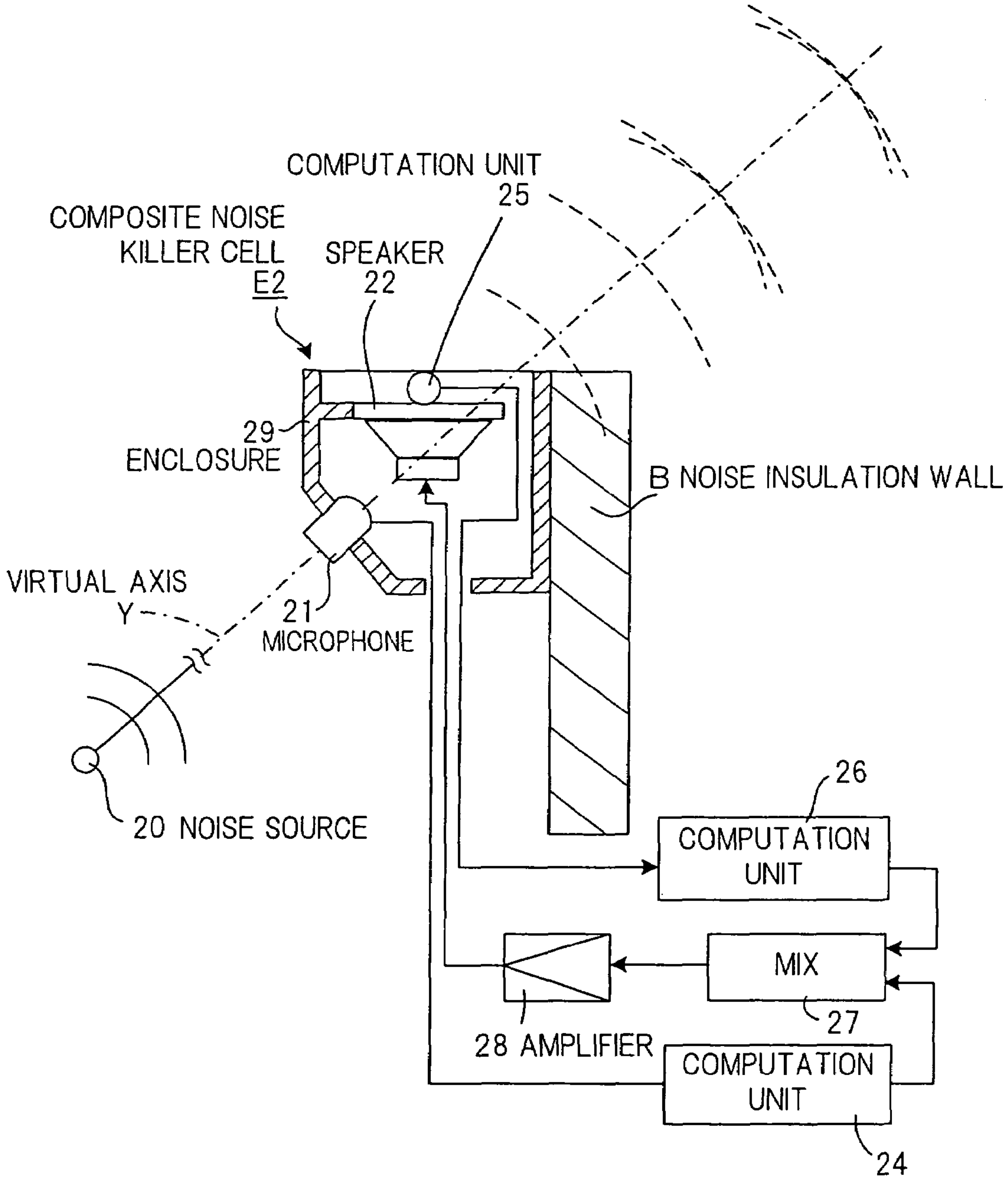
FIG. 25 is an explanation drawing conceptually showing an active acoustic control cell having composite killer functions used in the embodiment illustrated in FIG. 24.

Details of the structure of the composite noise killer cell E2 will be described based on FIG. 25. FIG. 25 is an explanation drawing conceptually showing the composite noise killer cell E2 in an extracted form. As shown in the drawing, the composite noise killer cell E2 has a microphone 21, a speaker 22 and a computation unit 24 which function in the same manner as in the noise killer cell E1. Also, another microphone 25 is provided ahead of the speaker 22 to measure the sound pressure of noise leaking to the outside after diffracting at the noise insulation wall B. The output signal of the microphone 25 is subjected to a predetermined computation by a computation unit 26. An electric signal based on the results of this computation drives the speaker 22 via a mixer 27 and an amplifier 28. On this occasion, the computation unit 26 drives the speaker 22 so that the sound pressure at the microphone 25 is reduced to zero. That is, the microphone 25, computation unit 26 and speaker 22 act integrally as an active acoustic control cell as well. At this time, the mixer 27 mixes signals computed by the computation units 24 and 26, so that the speaker 22 is driven by the resulting mixed signal. Hence, a sound wave produced by the speaker 22 can interfere with a sound wave, which travels rectilinearly from a noise source 20 past an upper end portion of the noise insulation wall B and diffuses to the outside, to decrease the sound wave, and can also decrease a diffracted wave diffracting at the noise insulation wall B and leaking to the outside.

According to the twentieth embodiment, therefore, noise passing beside the upper end portion of the active noise insulation wall and traveling rectilinearly (i.e., noise traveling along a virtual axis Y indicated by a one-dot chain line in FIG. 25) can be reduced by the rectilinear wave decreasing function of the composite noise killer cell E2. Furthermore, sound waves leaking as diffracted waves can be decreased by the diffracted sound reducing function of the composite noise killer cell E2 and the function of the active acoustic control cell A. That is, satisfactory noise reduction can be achieved in a wide range, including areas above the noise insulation wall B8, in the same manner as in the nineteenth embodiment.

Figure 26:
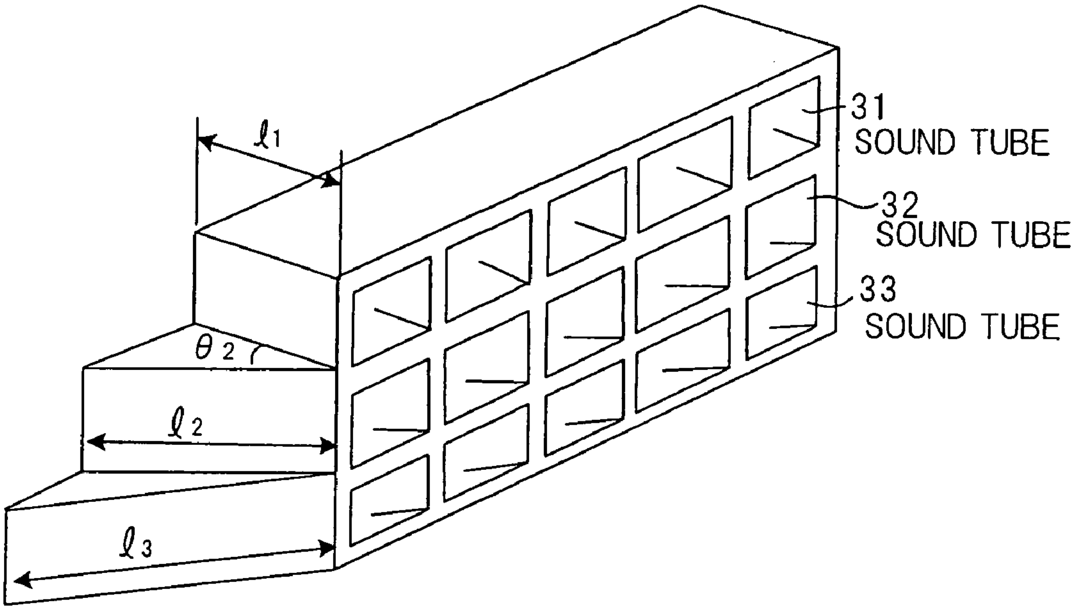
FIG. 26 is an explanation drawing conceptually showing another example of the noise killer cell used in the embodiment illustrated in FIG. 21.

The noise killer cell E1 and the composite noise killer cell E2 can be combined with the first to sixteenth embodiments and all of their modifications. Any of these combinations can reduce diffracted sounds, and noises traveling rectilinearly from the noise source and leaking to the outside of the noise insulation wall. Moreover, the noise killer cell E1 is designed to actively reduce noise traveling rectilinearly from the noise source, but may be a passive reducer. A passive noise killer cell E3 can be constituted, for example, from an interference type muffler as shown in FIG. 26. As illustrated in FIG. 26, the noise killer cell E3 is composed of sound tubes 31, 32, 33, tubes through which sound waves of lengths $l_1$, $l_2$ and $l_3$ pass. Here, $l_1<l_2<l_3$, and the sound tubes 32 and 33 at lower positions have progressively increasing lengths. Also, the sound tube 32 with the length $l_2$ is installed at an angle of $\theta_2$ satisfying $l_1=l_2 \cos \theta_2$ with respect to the length direction of $l_1$. Similarly, the sound tube 33 with the length $l_3$ is installed at an angle of $\theta_3$ satisfying $l_1=l_3 \cos \theta_3$ with respect to the length direction of $l_1$. By so doing, the entire widths of the sound tubes 31, 32 and 33 are made constant. Thus, sound waves passing through the sound tubes 31, 32, 33 of the noise killer cell E3 propagate as plane waves in a direction perpendicular to the sound wave output plane. As a result, displacements of the wave surface between the rectilinear wave and the delayed wave can be formed, and the interference of both waves can form a sound reduction region of the rectilinear wave.

The active sound reduction apparatuses used in the active noise insulation walls according to the nineteenth to twentieth embodiments may be any combinations of the active sound reduction apparatuses usable in the first to fourteenth embodiments. If there are a plurality of rows other than rows formed from the noise killer cells E1, E3 or the composite noise killer cells E2, active sound reduction apparatuses of different types may, of course, be disposed in respective rows.

Nor are there any restrictions on the structure of the noise insulation wall used in the active noise insulation wall according to the nineteenth or twentieth embodiment, i.e., the noise insulation wall combined with the noise killer cell. For example, as shown in FIG. 20, there may be a branch wall acting as a mere noise insulation wall on which the noise killer cell E1 or the like is not disposed. In this case as well, a sound reducing function at a portion corresponding to the branch wall B113 (see FIG. 20) is added, so that more effective noise insulation can be performed.

While the present invention has been described in the foregoing fashion, it is to be understood that the invention is not limited thereby, but may be varied in many other ways. Such variations are not to be regarded as a departure from the spirit and scope of the invention, and all such modifications as would be obvious to one skilled in the art are intended to be included within the scope of the appended claims.

What is claimed is:

1. An active noise insulation wall having a plurality of active sound reduction apparatuses, each such apparatus comprising;

an active acoustic control cell, disposed on an upper end surface of a noise insulation wall, for controlling a coming noise such that a diffracted sound pressure component of the coming noise at the upper end surface is actively reduced; and at least one sound tube of a length determined based on a wave length of a sound wave to be decreased by the at least one sound tube, the at least one sound tube being provided on a side of the active acoustic control cell facing a sound source to be subjected to sound reduction, or on a side of the active acoustic control cell opposite to the sound source, or on both of the sound source side and the opposite side of the active acoustic control cell;

the active sound reduction apparatuses being disposed in a row along a longitudinal direction of an upper end surface of a noise insulation wall or a side surface of an upper portion of the noise insulation wall, and wherein the at least one sound tube has a bottom portion buried in a depression formed in the noise insulation wall while maintaining a thickness of the noise insulation wall.

2. An active noise insulation wall as in claim 1, wherein the bottom portion of the at least one sound tube is buried in a depression formed in an upper surface of the noise insulation wall.

3. An active noise insulation wall as in claim 1, wherein the noise insulation wall branches at an upper end portion thereof to have a plurality of branch walls extending upward, and the active sound reduction apparatus is disposed either between two of the branch walls, or on a side of one of or the plurality of the branch walls facing a noise source, or on a side thereof opposite to the noise source.

4. An active noise insulation wall, comprising:

a plurality of rows formed by spacing adjacent rows by a predetermined distance, each of the rows being formed from a plurality of active sound reduction apparatuses, the plurality of active sound reduction apparatus in one row being spaced apart from the plurality of active sound reduction apparatus in an adjacent row, each such apparatus including, an active acoustic control cell, disposed on an upper end surface of a noise insulation wall, for controlling a coming noise such that a diffracted sound pressure component of the coming noise at the upper end surface is actively reduced, and one sound tube or a plurality of sound tubes of a length which is nearly ¼ of a wavelength or wavelengths of one sound wave or a plurality of sound waves other than a control target frequency of the active acoustic control cell, the one sound tube or the plurality of sound tubes being provided on a side of the active acoustic control cell facing a sound source to be subjected to sound reduction, or on a side of the active acoustic control cell opposite to the sound source, or on both of the sound source side and the opposite side of the active acoustic control cell, wherein the plurality of active sound reduction sound apparatuses is disposed in a longitudinal direction of the noise insulation wall.

5. An active noise insulation wall as in claim 4, further comprising:

noise killer cells, disposed on one of the rows facing a noise source, for generating a sound wave interfering with a sound wave traveling rectilinearly from the noise source after passing over an upper end portion of the noise insulation wall to decrease the sound wave traveling rectilinearly.

6. An active noise insulation wall as in claim 4, further comprising:

composite noise killer cells, having functions of a noise killer cell and the active acoustic control cell, are disposed on one of the rows facing a noise source, the noise killer cell being adapted to generate a sound wave interfering with a sound wave traveling rectilinearly from the noise source after passing over an upper end portion of the noise insulation wall to decrease the sound wave traveling rectilinearly.

7. An active noise insulation wall, comprising:

a plurality of rows formed by spacing the adjacent rows by a predetermined distance, each of the rows being formed from a plurality of active sound reduction apparatuses, the plurality of active sound reduction apparatus in one row being spaced apart from the plurality of active sound reduction apparatus in an adjacent row, each such apparatus including, an active acoustic control cell, disposed on an upper end surface of a noise insulation wall, for controlling a coming noise such that a diffracted sound pressure component of the coming noise at the upper end surface is actively reduced, and one acoustic resonator or a plurality of acoustic resonators tuned to a frequency or frequencies other than a control target frequency of the active acoustic control cell in order to decrease a sound pressure at the frequency or frequencies, the one acoustic resonator or the plurality of acoustic resonators being provided on a side of the active acoustic control cell facing a sound source to be subjected to sound reduction, or on a side of the active acoustic control cell opposite to the sound source, or on both of the sound source side and the opposite side of the active acoustic control cell, wherein the plurality of active sound reduction apparatuses is disposed in a longitudinal direction of the noise insulation wall.

8. An active noise insulation wall as in claim 7, further comprising:

noise killer cells, disposed on one of the rows facing a noise source, for generating a sound wave interfering with a sound wave traveling rectilinearly from the noise source after passing over an upper end portion of the noise insulation wall to decrease the sound wave traveling rectilinearly.

9. An active noise insulation wall as in claim 7, further comprising;

composite noise killer cells, having functions of a noise killer cell and the active acoustic control cell, are disposed on one of the rows facing a noise source, the noise killer cell being adapted to generate a sound wave interfering with a sound wave traveling rectilinearly from the noise source after passing over an upper end portion of the noise insulation wall to decrease the sound wave traveling rectilinearly.

10. An active noise insulation wall having a plurality of rows formed by spacing the adjacent rows by a predetermined distance, each of the rows being formed from a plurality of active acoustic control cells, disposed in a longitudinal direction of a noise insulation wall, for controlling a coming noise such that a diffracted sound pressure component of the coming noise at an upper end surface of the noise insulation wall is actively reduced, wherein, the plurality of acoustic control cells in one row is spaced apart from the plurality of acoustic control cells in an adjacent row.

11. An active noise insulation wall as in claim 10, further comprising:

noise killer cells, disposed on one of the rows facing a noise source, for generating a sound wave interfering with a sound wave traveling rectilinearly from the noise source after passing over an upper end portion of the noise insulation wall to decrease the sound wave traveling rectilinearly.

12. An active noise insulation wall as in claim 10, further comprising:

composite noise killer cells, having functions of a noise killer cell and the active acoustic control cell, are disposed on one of the rows facing a noise source, the noise killer cell being adapted to generate a sound wave interfering with a sound wave traveling rectilinearly from the noise source after passing over an upper end portion of the noise insulation wall to decrease the sound wave traveling rectilinearly.

* * * * *